United States Patent
Güthner et al.

(10) Patent No.: US 12,351,543 B2
(45) Date of Patent: Jul. 8, 2025

(54) PROCESS FOR THE PREPARATION OF A METASTABLE CRYSTAL MODIFICATION OF N-(AMINOIMINOMETHYL)-2-AMINOETHANOIC ACID (IV)

(71) Applicant: Alzchem Trostberg GmbH, Trostberg (DE)

(72) Inventors: Thomas Güthner, Trostberg (DE); Franz Thalhammer, Trostberg (DE); Jürgen Sans, Trostberg (DE)

(73) Assignee: Alzchem Trostberg GmbH, Trostberg (DE)

( * ) Notice: Subject to any disclaimer, the term of this patent is extended or adjusted under 35 U.S.C. 154(b) by 850 days.

(21) Appl. No.: 17/626,648

(22) PCT Filed: Jun. 25, 2020

(86) PCT No.: PCT/EP2020/067842
§ 371 (c)(1),
(2) Date: Jan. 12, 2022

(87) PCT Pub. No.: WO2021/008846
PCT Pub. Date: Jan. 21, 2021

(65) Prior Publication Data
US 2022/0289670 A1    Sep. 15, 2022

(30) Foreign Application Priority Data

Jul. 12, 2019  (DE) .................... 10 2019 118 893.8
Jul. 12, 2019  (DE) .................... 10 2019 118 894.6

(51) Int. Cl.
C07C 279/14    (2006.01)
A23K 20/142    (2016.01)
C07C 277/08    (2006.01)

(52) U.S. Cl.
CPC .......... *C07C 279/14* (2013.01); *A23K 20/142* (2016.05); *C07C 277/08* (2013.01); *C07B 2200/13* (2013.01)

(58) Field of Classification Search
None
See application file for complete search history.

(56) References Cited

U.S. PATENT DOCUMENTS 2,620,354 A    12/1952    Vassel et al.
2,654,779 A    10/1953    Vassel et al.
(Continued)

FOREIGN PATENT DOCUMENTS

BR    PI1010933 A2    4/2016
CN    101525305 A    9/2009
(Continued)

OTHER PUBLICATIONS

Strecker, M., "Organische Chemie. and Organische Basen", 1861, pp. 530-531.
(Continued)

*Primary Examiner* — Sudhakar Katakam
*Assistant Examiner* — Jennifer C Sawyer
(74) *Attorney, Agent, or Firm* — Kilpatrick Townsend & Stockton LLP

(57) ABSTRACT

The present invention relates to a method for preparing N-(aminoiminomethyl)-2-aminoacetic acid comprising N-(aminoiminomethyl)-2-aminoacetic acid in a thermodynamically metastable crystal modification.

7 Claims, 11 Drawing Sheets

(56) References Cited

U.S. PATENT DOCUMENTS

| | | | |
|---|---|---|---|
| 5,149,873 | A | 9/1992 | Hakansson et al. |
| 6,083,549 | A | 7/2000 | Harada et al. |
| 11,512,047 | B2 | 11/2022 | Güthner et al. |
| 2007/0231370 | A1 | 10/2007 | Gastner et al. |
| 2010/0028280 | A1 | 2/2010 | Philippe et al. |
| 2010/0055182 | A1 | 3/2010 | Gastner et al. |
| 2010/0143703 | A1 | 6/2010 | Winkler et al. |
| 2012/0225371 | A1 | 9/2012 | Kim et al. |
| 2014/0155646 | A1 | 6/2014 | Mrzena et al. |
| 2022/0388948 | A1 | 12/2022 | Guthner et al. |

FOREIGN PATENT DOCUMENTS

| | | | |
|---|---|---|---|
| CN | 101778574 | A | 7/2010 |
| CN | 105503659 | A | 4/2016 |
| CN | 105777594 | A | 7/2016 |
| CN | 106361736 | A | 2/2017 |
| DE | 00010005344 | | 12/1951 |
| DE | 964590 | C | 5/1957 |
| DE | 102007004781 | A1 | 8/2008 |
| DE | 102007053369 | A1 | 7/2009 |
| EP | 0441760 | A1 | 8/1991 |
| JP | 6054320 | A | 3/1985 |
| JP | 2014094999 | A | 5/2014 |
| JP | 2018063208 | A | 4/2018 |
| JP | 2022540331 | A | 9/2022 |
| RU | 2341972 | C2 | 12/2008 |
| WO | 2000059528 | A1 | 10/2000 |
| WO | 2005120246 | A1 | 12/2005 |
| WO | 2007135297 | A2 | 11/2007 |
| WO | 2008092591 | A2 | 8/2008 |
| WO | 2009012960 | A2 | 1/2009 |
| WO | 2010133618 | A1 | 11/2010 |
| WO | 2017149300 | A1 | 9/2017 |

OTHER PUBLICATIONS

Berthou et al., "Structure Cristalline et Moleculaire de la Glycocyamine", Acta Crystallographica, vol. B32, 1976, pp. 1529-1532.

De Miranda et al., "Study on Guanidino-Carboxylate Interactions in Copper(II) Ternary Complexes of Guanidinoacetic Acid with Glutamic and Aspartic Acids", Polyhedron, vol. 22, Issue 2, Jan. 15, 2003, pp. 225-233.

German Application No. DE102019118893.8, Search Report mailed Feb. 7, 2020, 7 pages.

German Application No. DE102019118894.6, Search Report mailed Feb. 7, 2020, 7 pages.

Du et al., "Self-Antibacterial UV-Curable Waterborne Polyurethane with Pendant Amine and Modified by Guanidinoacetic Acid", Journal of Materials Science, vol. 53, No. 1, Jan. 2018, pp. 215-229.

International Application No. PCT/EP2020/067837, International Search Report and Written Opinion mailed Jul. 31, 2020, 13 pages.

International Application No. PCT/EP2020/067839, International Search Report and Written Opinion mailed Jan. 21, 2021, 7 pages.

Wang et al., "Solid State Studies of the Assembly of Diionic Guanidinium/Carboxylate Compounds", Tetrahedron Letters, vol. 56, No. 21, May 20, 2015, pp. 2684-2687.

U.S. Appl. No. 17/625,494, Non-Final Office Action mailed May 11, 2022, 5 pages.

International Application No. PCT/EP2020/067837, International Preliminary Report on Patentability mailed Jan. 27, 2022, 8 pages.

International Application No. PCT/EP2020/067842, International Search Report and Written Opinion mailed Jan. 21, 2021, 9 pages.

International Application No. PCT/EP2020/067842, International Preliminary Report on Patentability mailed Nov. 30, 2021, 6 pages.

International Application No. PCT/EP2020/067839, International Preliminary Report on Patentability mailed Jan. 5, 2022, 7 pages.

U.S. Appl. No. 17/621,023, Corrected Notice of Allowance mailed Dec. 20, 2024, 5 pages.

U.S. Appl. No. 17/621,023, Notice of Allowance mailed Dec. 18, 2024, 7 pages.

Sharma, et al., "Polymorphism in Pharmaceutical Compounds", Conference: Advancements and Futuristic Trends in Material Science, Jan. 2011, pp. 39-48.

"Experimental Chemistry Lecture 1: Basic operation I", Edited by The Chemical Society of Japan, 4th edition, 2nd print, 1996, pp. 184-186.

Asahara, et al., "Solvent Handbook, Kodansha Ltd.", 1985, pp. 47-51.

Bernstein, "Polymorphism of Molecular Crystals", Bioavailability, 2007, pp. 335-337.

Ghasemzadeh, et al., "γ-Fe2O3@SiO2-EC-ZnII: A Magnetic Recyclable Nanocatalyst for the Synthesis of Spiro[indoline- 3,9'-xanthene]trione Derivatives in Aqueous Media", ChemistrySelect, vol. 3, No. 11, 2018, pp. 3161-3170.

Hirayama, et al., "Organic Compound Crystal Preparation Handbook", pp. 17-23, 37-40, 45-51 and 57-65.

Kukes, "Clinical Pharmacokinetics: Theoretical, Applied and Analytical Aspects", Therapy Pharmacology, 2009, pp. 234-248.

Sarma, et al., "Solid Forms of Pharmaceuticals: Polymorphs, Salts and Cocrystals", Korean Journal of Chemical Engineering, vol. 28, No. 2, Jan. 31, 2011, pp. 315-322.

Takada, et al., "API Form Screening and Selection in Drug Discovery Stage", Pharm Stage, vol. 6, No. 10, Jan. 15, 2007, pp. 20-25.

Variankaval, et al., "From Form to Function: Crystallization of Active Pharmaceutical Ingredients", American Institute of Chemical Engineers Journal, vol. 54, No. 7, Jun. 3, 2008, pp. 1682-1686.

International Application No. PCT/EP2020/067839, International Search Report and Written Opinion mailed Aug. 7, 2020, 14 pages.

U.S. Appl. No. 17/625,494, Notice of Allowance mailed Aug. 1, 2022, 8 pages.

Caira, "Crystalline Polymorphism of Organic Compounds", Topics In Current Chemistry, vol. 198, Jan. 1, 1998, pp. 163-208.

Thiyagaraj et al., "Synthesis, Growth of Semiorganic TGDCC (Tetra Glycine Dihydrated Calcium Chloride) Single Crystal and a Study of Effect by Urea on the Structural and Optical Properties", IOSR Journal of Applied Physics (IOSR-JAP), vol. 4, No. 2, Jul.-Aug. 2013, pp. 25-30.

Korean Application No. 10-2021-7041906, Office Action mailed Oct. 23, 2023, 4 pages.

Guha, "The Crystal and Molecular Structure of Glycocyamine", Acta Crystallographica, vol. 29, No. 10, Oct. 1, 1973, pp. 2163-2166.

Jones et al., "Conformations of GABA Analogues. I: Crystal and Molecular Structure of Guanidinoacetic Acid", Journal of Crystal and Molecular Structure, vol. 9, No. 5, Oct. 1, 1979, pp. 273-279.

Singh et al., "Determination of formation constants of some mixed complexes of glycocymin and Nitrilotriacetic acid by paper electrophoresis (Cu(II), UO2(II), Co(II), Zn(II), Cd(II)-Nitrilotriacetic acid-Glycocymin System)", Oriental Journal of Chemistry, vol. 24(1), 2008, pp. 283-286.

International Application No. PCT/EP2020/067842, International Search Report and Written Opinion mailed Aug. 10, 2020, 12 pages.

German Application No. 10 2019 118 894.6, German Search Report mailed Jul. 2, 2020, 7 pages.

German Application No. 10 2019 118 893.8, German Search Report mailed Jul. 2, 2020, 7 pages.

Nozaki, et al., "The Solubility of Amino Acids, Diglycine, and Triglycine in Aqueous Guanidine Hydrochloride Solutions", The Journal of Biological Chemistry, vol. 245, No. 7, Apr. 10, 1970, pp. 1648-1652.

PROCESS FOR THE PREPARATION OF A METASTABLE CRYSTAL MODIFICATION OF N-(AMINOIMINOMETHYL)-2-AMINOETHANOIC ACID (IV)

CROSS REFERENCE TO RELATED APPLICATION

This application is a U.S. national phase of International Patent Application No. PCT/EP2020/067842 filed on Jun. 25, 2020, which claims priority to German Patent Application Nos. 10 2019 118 894.6 and 10 2019 118 893.8, both filed in Germany on Jul. 12, 2019. The entire contents of all applications are hereby incorporated herein by this reference.

The present invention relates to a method for preparing N-(aminoiminomethyl)-2-aminoacetic acid comprising N-(aminoiminomethyl)-2-aminoacetic acid in a thermodynamically metastable crystal modification.

N-(aminoiminomethyl)-2-aminoacetic acid (CAS No. 352-97-6, molecular formula $C_3H_7N_3O_2$), also known as N-(aminoiminomethyl)-2-aminoethanoic acid, guanidinoacetic acid, guanidinoacetate, glycocyamine, N-amidinoglycine or N-(aminoiminomethyl)-glycine, is a guanidinocarboxylic acid with multiple applications, including in the synthesis of chemical products, in particular pharmaceuticals (cf. WO 2000/059528), for direct use as a pharmaceutical agent in renal diseases (cf. JP 60054320) or neurodegenerative diseases (cf. CN 106361736), in the preparation of polymers (cf. Du, Shuo et. al., Journal of Materials Science (2018), 53(1), 215-229), as a complexing agent for metals (cf. Lopes de Miranda et. al., Polyhedron (2003), 22(2), 225-233 or Singh, Padmakshi et. al, Oriental Journal of Chemistry (2008), 24(1), 283-286) and as an additive for the feeding of animals, in particular mammals, fish, birds (cf. WO 2005/120246) and humans (cf. WO 2008/092591, DE 10 2007 053 369).

N-(aminoiminomethyl)-2-aminoacetic acid can be prepared, for example, according to Strecker, M. (Jahresber. Fortschr. Chem. Verw. (1861), 530) from glycine by reaction with cyanamide. Alternatively, N-(aminoiminomethyl)-2-aminoacetic acid can be prepared, for example, by reacting glycine with S-methylisothiourea iodide using potassium hydroxide as base (cf. U.S. Pat. No. 2,654,779). The reaction of chloroacetic acid with ammonia to give glycine hydrochloride and its further reaction with cyanamide have also been described (cf. U.S. Pat. No. 2,620,354). In addition, the synthesis from chloroacetic acid and guanidine hydrochloride with the addition of sodium hydroxide solution is known (cf. CN 101525305).

In the known processes, N-(aminoiminomethyl)-2-aminoacetic acid is obtained as a fine crystalline powder which has a considerable dust content, i.e. a considerable proportion of particles which have a particle size of less than 63 µm.

For the handling of chemical products in solid form, it is often desirable for them to be in crystalline, granular, free-flowing, dust-free form with little or no fines. In particular, a poorly free-flowing, dusting powder is completely unsuitable for use as a feed additive.

To address this issue, it has been proposed, for example, to transform N-(aminoiminomethyl)-2-aminoacetic acid into mouldings, granules or extrudates (cf. WO 2009/012960) with the addition of polymeric binders (e.g. methyl cellulose) in amounts of 0.05 to 15% by weight and with the addition of water. A disadvantage of this process is that addition of a foreign substance, namely a binder, is absolutely necessary, and that the granules or mouldings have to be produced in an additional process step, using a special, technically complex and expensive apparatus, such as an extruder, granulator, intensive mixer or ploughshare mixer, and subsequent drying.

A further disadvantage of the process according to the above state of the art is that mouldings or granules either have a high binder content and thus a low dissolution rate, or dissolve relatively quickly with a low binder content, but at the same time have low strength and high abrasion values, so that absence of dust can no longer be guaranteed.

It was therefore the object of the invention to provide a process for the preparation of N-(aminoiminomethyl)-2-aminoacetic acid in the form of free-flowing, non-dusting crystal aggregates which do not have the disadvantages of the prior art, but can be prepared simply and with widely used standard apparatuses of the chemical industry, and which also have a high solubility.

These objects are achieved by a process for the preparation of N-(aminoiminomethyl)-2-aminoacetic acid comprising N-(aminoiminomethyl)-2-aminoacetic acid in a thermodynamically metastable crystal modification according to claim 1. Preferred embodiments of the invention are given in the subclaims, which may optionally be combined with one another.

The occurrence of chemical substances in different crystal forms or crystal modifications (polymorphism) is of great importance both for the production and application of the substances and for the development of formulations. Thus, the various crystal modifications of a chemical compound differ not only in appearance (crystal habit) but also in numerous other physical or physicochemical properties. It is not yet possible to predict the occurrence and number of crystal modifications including their physical or physicochemical properties. Especially the thermodynamic stability and also the different behavior after administration in living organisms cannot be determined in advance.

Under given pressure and temperature conditions, different polymorphic crystal modifications usually have different lattice energies or standard heats of formation. The crystal form with the lowest energy is called the stable form. Forms with higher energetic level, if they can be isolated, are called metastable (under the given pressure and temperature conditions). Metastable polymorphs have a tendency to transform into the stable polymorph. Due to the metastability, this requires the expenditure of an activation energy, e.g. by the effect of heat, mechanical energy or the influence of a solvent.

Moreover, it is generally known that different modifications of a substance can be monotropic or enantiotropic. In the case of monotropic polymorphism, a crystal form or crystal modification can represent the thermodynamically stable phase over the entire temperature range up to the melting point, whereas in enantiotropic systems there is an conversion point at which the stability behavior is reversed.

In the context of the present invention, it was found that N-(aminoiminomethyl)-2-aminoacetic acid, in addition to an already known thermodynamically stable crystal modification (hereinafter also referred to as form A or crystal form A), also occurs in a thermodynamically metastable crystal modification. This thermodynamically metastable crystal form according to the invention is also referred to hereinafter as form B or crystal form B.

This thermodynamically metastable crystal modification (form B) can be prepared by simple recrystallization of N-(aminoiminomethyl)-2-aminoacetic acid from water-containing solutions containing guanidine compounds. Surprisingly, it has also been shown in the underlying studies that this previously unknown, thermodynamically metastable crystal modification of N-(aminoiminomethyl)-2-aminoacetic acid can also be prepared by means of the direct synthesis of N-(aminoiminomethyl)-2-aminoacetic acid in solutions containing guanidine compounds.

Furthermore, it is surprising that this new metastable crystal modification form B is stable up to its melting point. A solid transformation from form B to form A or a reversible solid transformation form A/form B cannot be observed. Thus, form B is an example of monotropic polymorphism.

Thus, according to a first embodiment of the present invention, a process for the preparation of N-(aminoiminomethyl)-2-aminoacetic acid containing N-(aminoiminomethyl)-2-aminoacetic acid in a thermodynamically metastable crystal modification is an object of the present invention, in which N-(aminoiminomethyl)-2-aminoacetic acid is crystallized from a water-containing solution in the presence of at least one guanidine compound according to formula (I) or a salt thereof.

The guanidine compounds suitable for the inventive method are those of formula (I)

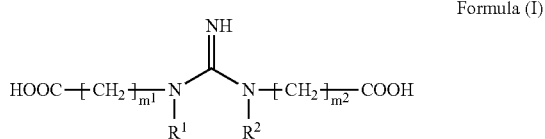

Formula (I)

where radicals $R^1$, $R^2$ as well as indices $m^1$, $m^2$ in formula (I) independently of one another mean:
  $R^1$, $R^2$=independently of one another hydrogen or C1 to C4 alkyl,
  $m^1$, $m^2$=independently of one another 1, 2 or 3, particularly 1.

C1 to C4 alkyl thereby particularly means methyl, ethyl, n-propyl, 2-methyl-ethyl, n-butyl, 2-methyl-propyl or 1-methyl-propyl. Especially preferred, C1 to C4 alkyl is methyl or ethyl.

These guanidine compounds can be used in neutral form, i.e. as a free acid or as a salt of said acid, particularly as alkaline earth salts or alkaline salts. Sodium salts, potassium salts, calcium salts and magnesium salts are particularly preferred. However, guanidine compounds according to formula (I) in neutral form are quite especially preferred.

The N-(aminoiminomethyl)-2-aminoacetic acid produced by this process may be present as a crystal mixture, namely a crystal mixture of form A and form B, or in pure form, namely 100% form B. Thus, according to a further embodiment of the present invention, it is also an object of the present invention to provide a process for preparing a thermodynamically metastable crystal modification of N-(aminoiminomethyl)-2-aminoacetic acid, in which N-(aminoiminomethyl)-2-aminoacetic acid is crystallized from a water-containing solution in the presence of at least one guanidine compound of formula (I). By means of this process, N-(aminoiminomethyl)-2-aminoacetic acid can be provided in pure form, namely 100% form B.

Furthermore, the present invention relates to a process for the preparation of a crystal mixture containing N-(aminoiminomethyl)-2-aminoacetic acid in a thermodynamically metastable crystal modification, in particular containing N-(aminoiminomethyl)-2-aminoacetic acid in a thermodynamically metastable crystal modification and N-(aminoiminomethyl)-2-aminoacetic acid in a stable crystal modification, in which N-(aminoiminomethyl)-2-aminoacetic acid is crystallized from a water-containing solution in the presence of at least one guanidine compound represented by formula (I).

According to the present invention, a crystal mixture is to be understood as a mixture comprising N-(aminoiminomethyl)-2-aminoacetic acid in crystalline form, wherein the N-(aminoiminomethyl)-2-aminoacetic acid a) consists of crystals of form A and crystals of form B, or b) consists of crystals having at least a first partial region which consists of form A and at least one second partial region which consists of form B, or c) consists of crystals of form A and crystals of form B and crystals which have at least one first partial region which consists of form A and have at least one second partial region which consists of form B.

According to the invention, a crystal mixture preferably has at least 10 wt %, more preferably at least 20 wt % and even more preferably at least 30 wt % of N-(aminoiminomethyl)-2-aminoacetic acid in form B. Preferred are crystal mixtures in which at least 50% by weight, more preferably at least 75% by weight and even more preferably at least 90% by weight of the N-(aminoiminomethyl)-2-aminoacetic acid is present in form B. Form B is characterized in particular by a crystal modification which, in the X-ray powder diffractogram using Cu—Kα radiation, has the strongest reflection bands at 2Θ(2 theta)=20.2° and 23.3° and 23.8° and 25.3° with a measurement accuracy of +/−0.2°.

The remaining portion of N-(aminoiminomethyl)-2-aminoacetic acid is present in the crystal mixtures according to the invention in another crystalline form, preferably in form A. Accordingly, the crystal mixtures preferably comprise at least 10% by weight, preferably at least 20% by weight and more preferably at least 30% by weight of N-(aminoiminomethyl)-2-aminoacetic acid in form A.

The water-containing solution used in these processes preferably contains at least 40% by weight, preferably at least 45% by weight and particularly preferably at least 50% by weight of water (based on the total weight of the solution).

Very preferably, water may be used as a solvent in the process.

Further preferably, N-(aminoiminomethyl)-2-aminoacetic acid can be dissolved in water or a water-containing solution in a first process step, and the N-(aminoiminomethyl)-2-aminoacetic acid containing N-(aminoiminomethyl)-2-aminoacetic acid in a thermodynamically metastable crystal modification can be crystallized in a second process step from the solution prepared in the first process step in the presence of the guanidine compound of formula (I).

It is also possible to use water or a water-containing solution containing a guanidine compound of formula (I) already in the first process step.

Alternatively preferably, however, the process can also be carried out in such a way that N-(aminoiminomethyl)-2-aminoacetic acid is prepared in a first process step from cyanamide and glycine in water or in a water-containing solution, and the N-(aminoiminomethyl)-2-aminoacetic acid containing N-(aminoiminomethyl)-2-aminoacetic acid in a thermodynamically metastable crystal modification is crystallized in a second process step from the reaction mixture prepared in the first process step in the presence of the guanidine compound of formula (I).

Thus, a process can be provided, wherein the desired product is obtained directly without subsequent recrystallization.

It is also possible to use water or a water-containing solution containing a guanidine compound of formula (I) already in the first process step, i.e. the reaction of cyanamide and glycine.

The product of crystallization in the presence of the guanidine compounds is a thermodynamically metastable crystal modification of N-(aminoiminomethyl)-2-aminoacetic acid, which in pure form shows the strongest reflection bands at 2 Θ(2 theta)=20.2° and 23.3° and 23.8° and 25.3° in the X-ray powder diffractogram of the crystal modification when Cu—Kα radiation is used, with a measurement accuracy of +/−0.2°.

As used herein and hereinafter, Cu—Kα radiation means copper K-alpha radiation of wavelength 1.5406 Å as commonly used in crystallographic studies.

The product of crystallization in the presence of the guanidine compounds is a thermodynamically metastable crystal modification of N-(aminoiminomethyl)-2-aminoacetic acid, which crystallizes in pure form in the orthorhombic space group $P2_12_12_1$ with Z=8, i.e. with two crystallographically independent molecules, and which in particular exhibits a pseudo-tetragonal packing. The unit cell has lattice constants a=7.7685 Å, b=7.7683 Å, c=17.4261 Å at 105 Kelvin with a measurement accuracy of +/−0.001 Å. The single crystal measurement was carried out with Mo—Kα radiation of wavelength 0.71073 Å at 105 K (Kelvin).

According to the present invention, an orthorhombic space group means a space group whose unit cell has three right angles (right angle=90°) and the three crystal axes a, b and c have different lengths.

According to a preferred embodiment, the present invention thus also relates to a process for the preparation of a thermodynamically metastable crystal modification of N-(aminoiminomethyl)-2-aminoacetic acid, which in pure form preferably shows in the X-ray powder diffractogram of the crystal modification when using Cu—Kα radiation the strongest reflection bands at 2Θ=20.2° and 23.3° and 23.8° and 25.3° with a measurement accuracy of +/−0.2°, and which is further preferably present in the orthorhombic space group $P2_12_12_1$, in particular in the orthorhombic polar space group $P2_12_12_1$ with Z=8, and which further preferably has a pseudo-tetragonal packing. The unit cell has lattice constants a=7.7685 Å, b=7.7683 Å, =17.4261 Å at 105 Kelvin with a measurement accuracy of +/−0.001 Å. The single crystal measurement was carried out with Mo—Kα radiation of wavelength 0.71073 Å at 105 K (Kelvin).

Under suitable crystallization conditions, this new crystal form B forms polygonal or spherical, radially radiating aggregates of acicular partial crystallites, which have a roundish habit and a largely uniform aggregate size. Thus, they ensure optimal handling as a solid by providing a dust-free, free-flowing product with no tendency to cake. Crystal modification B can be classified as low in dust, since the proportion of crystals with a grain size of <63 μm (mesh size) is below 10%, preferably below 5% (cf. examples). Due to its structure of fine, acicular partial crystallites, this habit of the new crystal form B of N-(aminoiminomethyl)-2-aminoacetic acid also ensures a higher dissolution rate. Additionally and quite unexpectedly, N-(aminoiminomethyl)-2-aminoacetic acid of crystal form B also offers a higher absolute solubility in water-containing media.

When N-(aminoiminomethyl)-2-aminoacetic acid is prepared by one of the known methods, especially from reaction mixtures containing water, the compound is obtained in the well known crystal form A. One and the same crystal structure has been described by three groups of authors: by Sankarananda Guha, Acta Cryst. B29 (1973), 2163 and by Par J. Berthou et. al. respectively, Acta Cryst B32 (1976), 1529 and by Wei Wang et. al, Tetrahedron Letters 56 (2015), 2684. In all three papers, N-(aminoiminomethyl)-2-aminoacetic acid (here called form A) is described as a monoclinic structure of space group $P2_1/n$ with Z=4 and approximate lattice constants a=4.95 Å, b=6.00 Å, c=17.2 Å, β=4.5°, with a cell volume of approx. 510 Å$^3$, whereby in Berthou et. al. the published space group $P2_1/c$ was transformed to the space group $P2_1/n$ via a coordinate transformation. The experimental crystal density of N-(aminoiminomethyl)-2-aminoacetic acid of form A is about 1.50 g/cm$^3$. The characteristic powder diffractogram of N-(aminoiminomethyl)-2-aminoacetic acid in form A is shown in FIG. 1. Using Cu—Kα radiation (copper K-alpha radiation), in particular, the band position 2Θ(2theta)=20.7° and 26.0° is characteristic of form A. The powder diffractogram agrees with the diffraction pattern calculated from the published single crystal structure data.

If N-(aminoiminomethyl)-2-aminoacetic acid is crystallized, recrystallized or prepared from conventional solvents, such as water, methanol, ethanol, isopropanol or mixtures of methanol, ethanol, ethanediol or acetonitrile with water, without a guanidine compound according to formula (I) being present, N-(aminoiminomethyl)-2-aminoacetic acid is obtained exclusively in crystal form A, as has been shown by experiments.

Surprisingly, it was found that N-(aminoiminomethyl)-2-aminoacetic acid is preferentially formed in crystal form B during crystallization from water or water-containing solutions containing guanidine compounds. This is all the more surprising since in the known synthesis of N-(aminoiminomethyl)-2-aminoacetic acid from chloroacetic acid and guanidine hydrochloride no further crystal forms are formed in addition to the known crystal form A (cf. examples).

N-(aminoiminomethyl)-2-aminoacetic acid of form B (pure form) is characterized by its powder diffractogram with Cu—Kα radiation (see FIG. 2), with bands at 2Θ(2theta)=20.2° and 25.3° and a weaker double reflection at 2Θ(2theta)=23.3 °/23.8° being characteristic. A single crystal X-ray structural analysis revealed for N-(aminoiminomethyl)-2-aminoacetic acid of form B the orthorhombic polar space group $P2_12_12_1$ with two crystallographically independent molecules, i.e., Z=8. The packing of the molecules exhibits a pseudo-tetragonal symmetry. The unit cell has lattice constants a=7.7685 Å, b=7.7683 Å, c=17.4261 Å at 105 Kelvin with a measurement accuracy of +/−0.001 Å. The single crystal measurement here was performed with Mo—Kα radiation of wavelength 0.71073 Å. The unit cell volume is 1052 Å$^3$ and the calculated X-ray crystal density is 1.479 g/cm$^3$ at 105 Kelvin.

The experimental crystal density of N-(aminoiminomethyl)-2-aminoacetic acid of form B is 1.41 g/cm$^3$+/−0.03 g/cm$^3$ at 20° C. Thus, the experimental crystal density of form B is significantly lower than that of crystal form A, which is 1.50 g/cm$^3$+/−0.03 g/cm$^3$ at 20° C. This difference in crystal density indicates a thermodynamic instability of form B compared to form A.

Crystal form B of N-(aminoiminomethyl)-2-aminoacetic acid is present in the form of spherical or polygonal, radially radiating aggregates with an outer roundish habit. The single crystals represent the finest needles from which the spherical aggregates are built up. This has the surprising advantage that form B can be used to provide a physical form of N-(aminoiminomethyl)-2-aminoacetic acid comprising spherical or polygonal, granular, abrasion-resistant aggregates, with a largely uniform aggregate size, excellent pourability and largely dust-free. Typical crystal aggregates of N-(aminoiminomethyl)-2-aminoacetic acid of form B are shown in FIG. 4. For comparison, conventional prior art N-(aminoiminomethyl)-2-aminoacetic acid of form A, which has the habit of matted, fine crystal needles, is shown in FIG. 3.

N-(aminoiminomethyl)-2-aminoacetic acid form A and form B also differ in the infrared spectrum. Characteristic of form A are stronger bands at 1005.9, 940.3 and 816.8 $cm^{-1}$, characteristic of form B are stronger bands at 1148.0, 997.7 and only a weak band at 815 $cm^{-1}$.

Furthermore, the two crystal forms show different melting and decomposition points in their pure form:

N-(aminoiminomethyl)-2-aminoacetic acid form A:
DSC onset 280.5° C., peak 286.3° C., heat of fusion 887+/−1 J/g.

N-(aminoiminomethyl)-2-aminoacetic acid form B:
DSC onset 272.5° C., peak 280.4° C., heat of fusion 860+/−1 J/g.

These data impressively show that N-(aminoiminomethyl)-2-aminoacetic acid form B is a thermodynamically metastable crystal modification, which is the thermodynamically more unstable form compared to form A, with the energy difference between the two forms being about 27 J/g and with the onset point of the melting regions showing a difference of 8 K.

Further investigations have shown that N-(aminoiminomethyl)-2-aminoacetic acid form B has a water solubility that is about 20% higher than that of N-(aminoiminomethyl)-2-aminoacetic acid form A, and that this fact applies in the temperature range between 5 and 95° C. (see FIG. 5). This effect is completely unpredictable.

In summary, it should be emphasized here that N-(aminoiminomethyl)-2-aminoacetic acid in crystal modification B, in particular prepared by crystallization of N-(aminoiminomethyl)-2-aminoacetic acid from a water-containing solution containing guanidine compounds, surprisingly combines advantageous and usually opposite properties, such as, for example, a coarse, free-flowing grain and at the same time a high dissolution rate, the formation of crystal aggregates without the addition of a binder, and provides an increased absolute solubility at a given temperature, despite identical chemical composition.

This new crystal modification is suitable for use as a feed additive for animals due to its excellent properties. Thus, a feed additive comprising the thermodynamically metastable crystal modification of N-(aminoiminomethyl)-2-aminoacetic acid described herein is also an object of the present invention. The feed additive is particularly suitable for poultry.

Such feed additives may be formulated as premixes. Thus, moreover, the use of the thermodynamically metastable crystal modification of N-(aminoiminomethyl)-2-aminoacetic acid described herein or crystal mixtures containing said crystal modification for the preparation of a feed additive is also an object of the invention.

Surprisingly, it has been shown in the underlying investigations that this previously unknown, thermodynamically metastable crystal modification of N-(aminoiminomethyl)-2-aminoacetic acid as well as N-(aminoiminomethyl)-2-aminoacetic acid containing this thermodynamically metastable crystal modification and crystal mixtures containing this thermodynamically metastable crystal modification can be prepared by direct synthesis of N-(aminoiminomethyl)-2-aminoacetic acid in water-containing solutions containing guanidine compounds.

Thus, the present invention also relates to a1) a process for the preparation of a thermodynamically metastable crystal modification of N-(aminoiminomethyl)-2-aminoacetic acid and a2) a process for the preparation of N-(aminoiminomethyl)-2-aminoacetic acid containing a thermodynamically metastable crystal modification and a3) a process for the preparation of a crystal mixture containing N-(aminoiminomethyl)-2-aminoacetic acid in a thermodynamically metastable crystal modification, in particular of a crystal mixture containing N-(amino-iminomethyl)-2-aminoacetic acid in a thermodynamically metastable crystal modification and N-(aminoiminomethyl)-2-aminoacetic acid in a thermodynamically stable crystal modification, wherein N-(aminoiminomethyl)-2-aminoacetic acid is prepared in a first process step from cyanamide and glycine in water or in a water-containing solution, and a1) the thermodynamically metastable crystal modification, or a2) the N-(aminoiminomethyl)-2-aminoacetic acid containing N-(aminoiminomethyl)-2-aminoacetic acid in a thermodynamically metastable crystal modification, or a3) the crystal mixture, is crystallized in a second process step from the reaction mixture prepared in the first process step in the presence of the guanidine compound of formula (I).

The said guanidine compounds of formula (I) can be used as individual substances or in combination, in particular also in combination of two or more different guanidine compounds of formula (I), in order to induce the formation of the thermodynamically metastable form B during the crystallization of N-(aminoiminomethyl)-2-aminoacetic acid. The added amounts of the guanidine compounds mentioned can vary within wide ranges.

Preferably, the guanidine compounds of formula (I) can be used in an amount corresponding to 80% of the maximum amount that can be dissolved in water at 25° C. under normal pressure. In this way it can be ensured that the guanidine compounds necessary for crystallization of form B are not included in the crystal structure during crystallization.

Further preferably, the guanidine compounds of formula (I) may be used in an amount of at least 0.01% by weight and at most 10% by weight (based on the total weight of the solution). Preferably, the guanidine compounds of formula (I) may be used in an amount of at least 0.1% by weight, more preferably at least 0.2% by weight, more preferably at least 0.3% by weight, more preferably at least 0.5% by weight, and very particularly preferably at least 1 wt. %, with further preferably at most 10 wt. % (in each case based on the total weight of the solution) being used. At the same time, the guanidine compound of formula (I) can be used in an amount of at most 10% by weight, further preferably of at most 5% by weight, preferably at most 3% by weight, particularly preferably at most 2.5% by weight and very especially preferably 2% by weight (in each case based on the total weight of the solution).

The higher the concentration of a defined guanidine compound according to the invention, the higher the content of form B in the crystallized product.

Thus, the present invention also relates to a1) a process for the preparation of a thermodynamically metastable crystal modification of N-(aminoiminomethyl)-2-aminoacetic acid and a2) a process for the preparation of N-(aminoiminomethyl)-2-aminoacetic acid containing a thermodynamically metastable crystal modification and a3) a process for the preparation of a crystal mixture containing N-(aminoiminomethyl)-2-aminoacetic acid in a thermodynamically metastable crystal modification, in particular of a crystal mixture containing N-(aminoimino-methyl)-2-aminoacetic acid in a thermodynamically metastable crystal modification and N-(aminoiminomethyl)-2-aminoacetic acid in a thermodynamically stable crystal modification, in which a water-containing solution is used and the amount of water is at least 40% by weight, preferably at least 50% by weight, preferably at least 60 wt. % water, preferably at least 70% by weight, further preferably at least 80% by weight water and particularly preferably at most 98% by weight (based on the total weight of the solution) and the amount of guanidine compound according to formula (I) is at least 0.01% by weight and at most 10% by weight (based on the total weight of the solution).

Further preferred is a process in which the glycine is provided in water or the water-containing solution containing at least one guanidine compound of formula (I) dissolved in a concentration of at least 0.01% by weight and at most 10% by weight, and the cyanamide is added. The addition of cyanamide may thereby further preferably be in the form of a solid or in the form of a solution, in particular an aqueous cyanamide solution.

As water-containing solutions, solutions can be used that are capable of dissolving glycine and cyanamide.

The water-containing solution provided for dissolving glycine can preferably contain at least 40% by weight of water, further preferably at least 50% by weight, further preferably at least 60% by weight and particularly preferably at least 70% by weight water as well as one or more, in particular up to 20 different, guanidine compounds according to formula (I) in concentrations of each individually 0.01 to 10% by weight, so that the sum of all guanidine compounds constitutes a proportion of 0.01 to 10% by weight. Glycine is dissolved therein in a concentration of 3 to 30 wt. % as well as other substances or mixtures (e.g. sodium hydroxide solution) which may contain water. The mixture before dosage of cyanamide has a water content of preferably 50 to 97% by weight. Cyanamide is preferably dosed as an aqueous solution, in particular with a concentration of 5 to 60% by weight, preferably 28 to 52% by weight (based on the aqueous cyanamide solution).

It is also recommended that the reactants of the reaction, namely cyanamide and glycine, be reacted and thus converted at a reaction temperature in the range of 20 to 100° C., preferably in the range of 60 to 100° C. This may take place at normal pressure, under vacuum or even under pressure. Preferably, the reaction can take place at normal pressure in a temperature range from 20 to 100° C.

However, it is also recommended that the reaction be carried out at a pH in the range of 7.0 to 10.0, preferably at a pH in the range of 8.0 to 10.0. The pH is adjusted with a suitable base, which may be both organic and inorganic bases. Preferably, sodium hydroxide, potassium hydroxide, calcium hydroxide, ammonia or water-containing solutions thereof may be used. Sodium hydroxide, calcium hydroxide and water-containing solutions thereof can be used with particular preference.

The reaction proceeds without complications under these conditions, whereby the product formed gradually forms in the reaction mixture and can already crystallize during the reaction. After the addition of cyanamide has been completed, the reaction mixture can continue to react for some time. As soon as the saturation point, i.e. the maximum concentration at the reaction temperature, is reached, crystallization begins. According to the process of the invention, crystal nucleation and crystallization preferably take place in form B, the presence of at least one of the mentioned guanidine compounds being considered essential to the invention.

Crystallization of the desired product may take place at a temperature in the range of −5 to 100° C.

Surprisingly, it was also found that the presence of guanidine compounds of formula (I) in the reaction mixture increases the solubility of N-(aminoiminomethyl)-2-aminoacetic acid, in some cases significantly, so that a larger mass of N-(aminoiminomethyl)-2-aminoacetic acid, moreover in crystal form B, is obtained from the water-containing solution. Preferably, the process can thus be carried out by crystallizing the N-(aminoiminomethyl)-2-aminoacetic acid in a temperature range from −40 to 100° C., in particular in a temperature range from −5 to 70° C., more preferably in a temperature range from −5 to 50° C., more preferably in a temperature range from −5 to 40° C.

However, a process in which crystallization takes place in a controlled manner is particularly preferred. Here, the reaction mixture is exposed to defined temperature differences in constant time intervals. In this way, a particularly uniform crystallization can be achieved.

Thus, a particularly preferred process is one in which N-(aminoiminomethyl)-2-aminoacetic acid is crystallized at a cooling rate in the range of 0.01 to 5 K/min, more preferably in the range of 0.1 to 5 K/min, more preferably in the range of 0.5 to 5 K/min, in a temperature range of −5 to 100° C.

In any case, ordinary stirred reactors are preferably used. The use of complex technical apparatus is not necessary.

After complete crystallization of the desired N-(aminoiminomethyl)-2-aminoacetic acid form B, the crystallized product is preferably filtered off by filtration, e.g. by means of a centrifuge, pressure suction filter, belt filter or filter press. To remove excess reactants and guanidine compounds, the product is preferably washed with the above-mentioned solvent or solvent mixture. Preferably, washing is done with water, whereby the temperature of the washing water is preferably 0 to 50° C.

Of course, in order to improve the economy of the process, it is possible to recycle the mother liquor obtained from the separation of the N-(aminoiminomethyl)-2-aminoacetic acid of crystal form B into the process, optionally by adding further guanine compound(s) and/or by increasing the concentration, e.g. by evaporation.

After drying, preferably in the temperature range of 40 to 100° C., the process according to the invention yields a dry, free-flowing, granular product consisting of radially radiating, polygonal or roundish aggregates. The crystal aggregates have an external dimension of 150 to 3,000 μm, preferably 300 to 1,500 μm and a dust content (i.e. particle content smaller than 63 μm) of less than 5% by weight.

The N-(aminoiminomethyl)-2-aminoacetic acid form B thus produced has a high purity, typically >99.0%, is easy to handle and shows hardly any mechanical abrasion. Due to these properties, the crystal form B of N-(aminoiminomethyl)-2-aminoacetic acid according to the invention is particularly suitable for the above-mentioned applications, in particular as a food additive or as a pharmaceutical agent.

Thus, according to a further thought, the present invention also relates to the use of a1) the thermodynamically metastable crystal modification of N-(aminoiminomethyl)-2-aminoacetic acid as well as a2) the N-(aminoiminomethyl)-2-aminoacetic acid containing a thermodynamically metastable crystal modification as well as a3) the crystal mixture containing N-(aminoiminomethyl)-2-aminoacetic acid in a thermodynamically metastable crystal modification, in particular a crystal mixture containing N-(aminoiminomethyl)-2-aminoacetic acid in a thermodynamically metastable crystal modification and N-(aminoiminomethyl)-

2-aminoacetic acid in a thermodynamically stable crystal modification, in each case for the preparation of a food supplement or for the preparation of a feed additive.

According to the present invention, N-(aminoiminomethyl)-2-aminoacetic acid can be provided in a thermodynamically metastable crystal modification, wherein the N-(aminoiminomethyl)-2-aminoacetic acid is completely, i.e. 100%, in form B.

Thus, a method for preparing a thermodynamically metastable crystal modification of N-(aminoiminoethyl)-2-aminoacetic acid is also an object of the present invention, whereby the thermodynamically metastable crystal modification has the orthorhombic space group $P2_12_12_1$ with Z=8 with the lattice constants a=7.7685 Å, b=7.7683 Å and c=17.4261 Å at 105 Kelvin and a measurement accuracy of +/−0.001 Å.

Alternatively, N-(aminoiminomethyl)-2-aminoacetic acid according to the present invention may be present as a crystal mixture, in which N-(aminoiminomethyl)-2-aminoacetic acid in form B and in form A are crystallized side by side in different crystals or side by side within a crystal.

Thus, it is also an object of the present invention to provide a crystal mixture containing N-(aminoiminomethyl)-2-aminoacetic acid in a thermodynamically stable crystal modification and N-(aminoiminomethyl)-2-aminoacetic acid in a thermodynamically metastable crystal modification.

Preferably, the crystal mixture contains N-(aminoiminomethyl)-2-aminoacetic acid in a thermodynamically stable crystal modification and N-(aminoiminomethyl)-2-aminoacetic acid in a thermodynamically metastable crystal modification in a weight ratio ranging from 0.1:9.9 to 9.9:0.1, more preferably in the range from 1:9 to 9:1, more preferably in the range from 1:4 to 9:1, more preferably in the range from 1:2 to 9:1 and particularly preferably from 1:1 to 9:1.

These crystal mixtures are excellently suited as feed additives for breeding and fattening animals due to their crystal properties. Thus, a feed additive for breeding and fattening animals comprising a crystal mixture containing N-(aminoiminomethyl)-2-aminoacetic acid in a thermodynamically stable crystal modification and N-(aminoiminomethyl)-2-aminoacetic acid in a thermodynamically metastable crystal modification is also an object of the present invention.

Particularly preferred is a feed additive in which the crystal mixture contains the N-(aminoiminomethyl)-2-aminoacetic acid in a thermodynamically stable crystal modification and the N-(aminoiminomethyl)-2-aminoacetic acid in a thermodynamically metastable crystal modification in a weight ratio ranging from 1:9 to 9:1.

The following examples will further explain the essence of the invention.

EXAMPLES

Guanidine Compounds Used

1) N,N-guanidinodiacetic Acid

Preparation of N,N-guanidinodiacetic Acid (CAS 94324-66-0)

Figure 1:
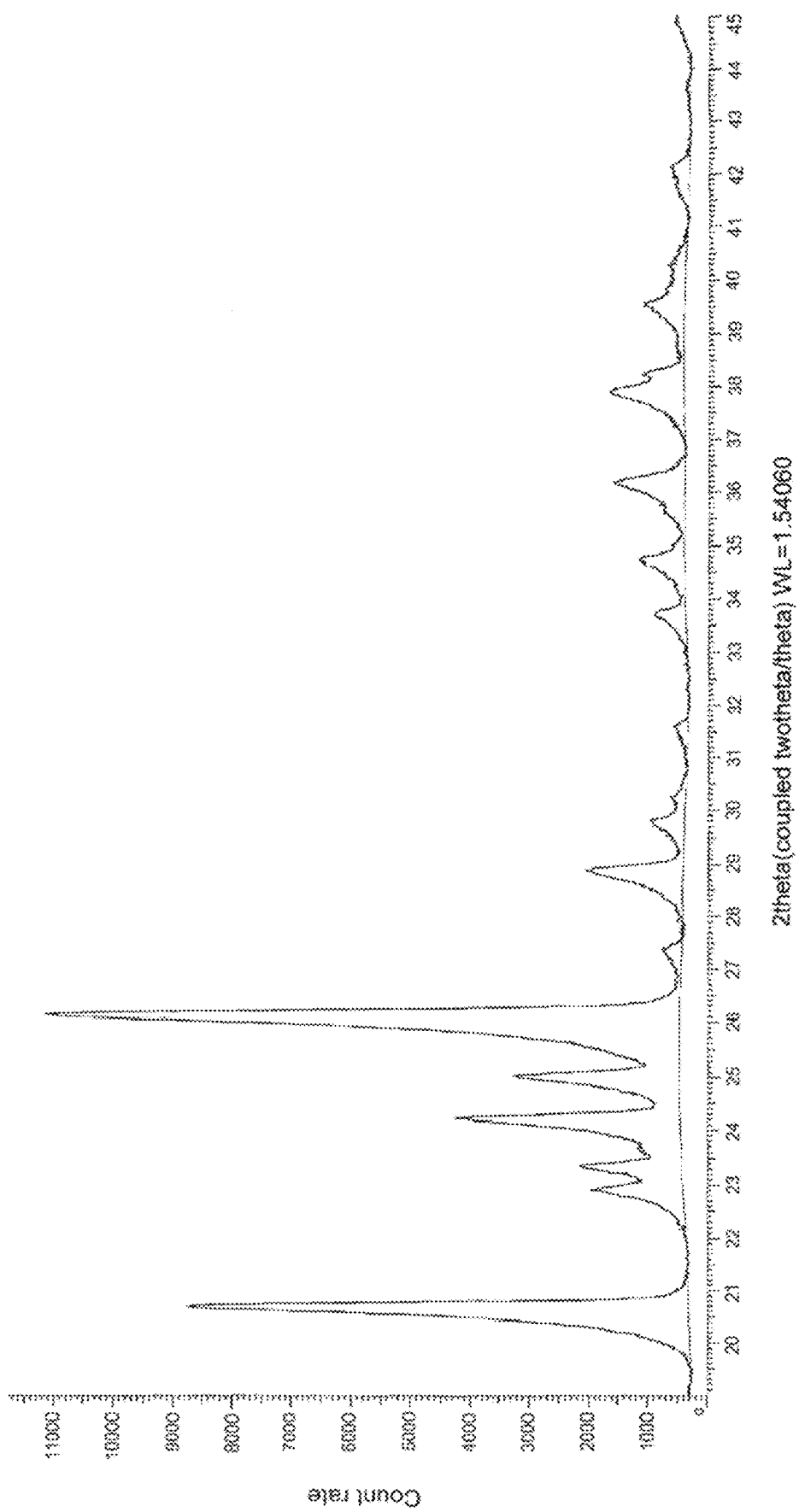
FIG. 1: X-ray powder diffractogram of N-(aminoiminomethyl)-2-aminoacetic acid of form A of Example 1

The synthesis was analogous to T. S. Leyh, Biochemistry 1985, 24, 308-316. 65.15 g (1.55 mol) cyanamide was dissolved in 65.15 g of water, to which was added 171.6 g (1.29 mol) of iminodiacetic acid and 325 ml of 25% ammonia solution and stirred for 96 hours at 22° C. Then, 628.7 g of 96% acetic acid was added to adjust the pH from 10.63 to 5.00. The thick suspension obtained was stirred overnight, then sucked off and washed with water. After drying at 40° C., 103.8 g of N,N-guanidinodiacetic acid was obtained with correct elemental analysis. The yield was 46.1%. NMR data in $d^6$-DMSO: $^1$H: 3.991 ppm, $^{13}$C: 171.2 ppm (carboxylate), 157.5 ppm (guanidine), 54.6 ppm ($CH_2$).

2) N,N'-guanidinodiacetic Acid

Preparation of N,N'-guanidinodiacetic Acid

2a.) 1242 g of a 20% sodium hydroxide solution (6.21 mol) were provided at 20° C. Into this, a total of 246 g (2.12 mol) of thiohydantoin was stirred in portions and hydrolyzed at 20° C. for 24 hours. The reaction mixture was diluted with 650 g of water, cooled to 5° C. and precipitated within 45 minutes with 638 ml of a 32% hydrochloric acid (6.55 mol). The precipitated solid was sucked off, washed 2 times with cold water of 5° C. and 1 time with cold ethanol of 5° C. After drying in vacuo at 40° C., thiohydantoic acid 202 g (71%) was obtained in the form of a yellowish solid. The purity determined by HPLC was >99%. The product had the following elemental composition: 26.95% C, 4.40% H, 20.90% N. The melting point was 170° C. under decomposition.

2b.) 167.8 g (1.25 mol) of thiohydantoic acid from Example 2a.) was provided in 210 ml of methanol at 40° C. Within 2 hours, 221.8 g (1.563 mol) of methyl iodide was added dropwise and stirred for 1 hour at 40° C. The obtained orange clear reaction mixture was evaporated completely in vacuo at 40° C. 345.13 g (1.25 mol) of S-methyl-isothio-hydantoic acid hydroiodide was obtained in the form of a brown viscous melt. The yield was quantitative. The reaction product was further reacted without analysis.

2c.) 345.13 g (1.25 mol) of S-methyl-isothiohydantoic acid hydroiodide from 2b.) were dissolved in 300 ml of water. In a reaction flask, 225 g (3.00 mol) of glycine was dissolved in 400 ml of water and 1253 ml of 25% aqueous ammonia solution (16.7 mol) was added. At 20° C., the solution of S-methyl-isothiohydantoic acid hydroiodide was dosed to the glycine solution over 4 hours. Then, post-stirring was carried out at 20° C. for 16 hours. A white suspension of pH 11.0 was obtained, which was cooled to 5° C. At 5° C., 1948 g of 32% hydrochloric acid (17.1 mol) was added dropwise to adjust the pH to 3.0. The white suspension obtained was sucked off, washed with water and ethanol and dried at 40° C. in vacuo. 140.6 g N,N'-guanidinodiacetic acid in the form of a white solid was obtained. The yield was 64.2%. The purity determined by HPLC was 96%. The elemental composition was: 34.07% C, 5.49% H, 23.20% N. The chloride content was 0.26%, the water content<0.1%. The substance had no melting point, but decomposed above 230° C., turning black.

Dissolved in $d_6$-DMSO, the following NMR spectra were obtained: $^{13}$C: 170.08 ppm (COOH), 157.11 ppm (guanidine-C), 54.40 ppm (CH$_2$); $^1$H: 7.2 ppm (broad, NH), 4.00 ppm (CH$_2$). Dissolved in D$_2$O and mixed with an equimolar amount of NaOD, i.e. as monosodium salt, the following NMR data were obtained: $^{13}$C: 175.44 ppm (COOH), 156.32 ppm (guanidine-C), 44.96 ppm (CH$_2$); $^1$H: approx. 7 ppm (very broad, NH), 4.80 ppm (CH$_2$).

3) N'-carboxymethyl-3-guanidinopropionic Acid 69.0 g (0.25 mol) of S-methyl-isothiohydantoic acid hydroiodide from synthesis example 2b.) was dissolved in 300 ml of water. In a reaction flask, 53.4 g (0.6 mol) of beta-alanine was dissolved in 400 ml of water and 250 ml of 25% aqueous ammonia solution (3.34 mol) was added. At 20° C., the solution of S-methyl-isothiohydantoic acid hydroiodide was dosed to the beta-alanine solution over 4 hours. Then, post-stirring was carried out at 20° C. for 16 hours. A white suspension of pH 10.9 was obtained, which was cooled to 5° C. At 5° C., 391 g of 32% hydrochloric acid (3.43 mol) was now added dropwise to adjust a pH of 3.0. The white suspension obtained was sucked off, washed with water and ethanol and dried at 40° C. in vacuo. 21.6 g N'-carboxymethyl-3-guanidinopropionic acid in the form of a white solid was obtained. The yield was 45.7%. The purity determined by HPLC was 94%.

4) N'-carboxymethyl-4-guanidinobutanoic Acid 69.0 g (0.25 mol) of S-methyl-isothiohydantoic acid hydroiodide from synthesis example 2b.) was dissolved in 300 ml of water. In a reaction flask, 61.8 g (0.6 mol) of 4-aminobutanoic acid was suspended in 400 ml of water and 250 ml of 25% aqueous ammonia solution (3.34 mol) was added, forming a solution. At 20° C., the solution of the S-methyl-isothiohydantoic acid hydroiodide was added over 4 hours to the solution of 3-aminobutanoic acid. Then, post-stirring was carried out at 20° C. for 16 hours. A white suspension of pH 10.8 was obtained, which was cooled to 5° C. At 5° C., 386 g of 32% hydrochloric acid (3.39 mol) was added dropwise to adjust the pH to 3.0. The white suspension obtained was sucked off, washed with water and ethanol and dried at 40° C. in vacuo. 23.7 g of N'-carboxymethyl-4-guanidinobutanoic acid was obtained in the form of a white solid. The yield was 46.7%. The purity determined by HPLC was 92%.

X-Ray Powder Diffraction Measurement

In the scope of the present examples, X-ray powder diffraction measurements were performed using a Bruker D2 Phaser powder diffractometer with theta/2theta geometry, a LYNXEYE detector, Cu—Kα radiation of wavelength 1.5406 Å with an accelerating voltage of 30 kV and an anode current of 10 mA, a nickel filter and an increment of 0.02°. The samples for examination were ground in an agate mortar and pressed onto the sample plate according to the manufacturer's instructions and the surface was smoothed.

Calibration Line for the Radiographic Determination of the Proportion Form A/B

Figure 9:
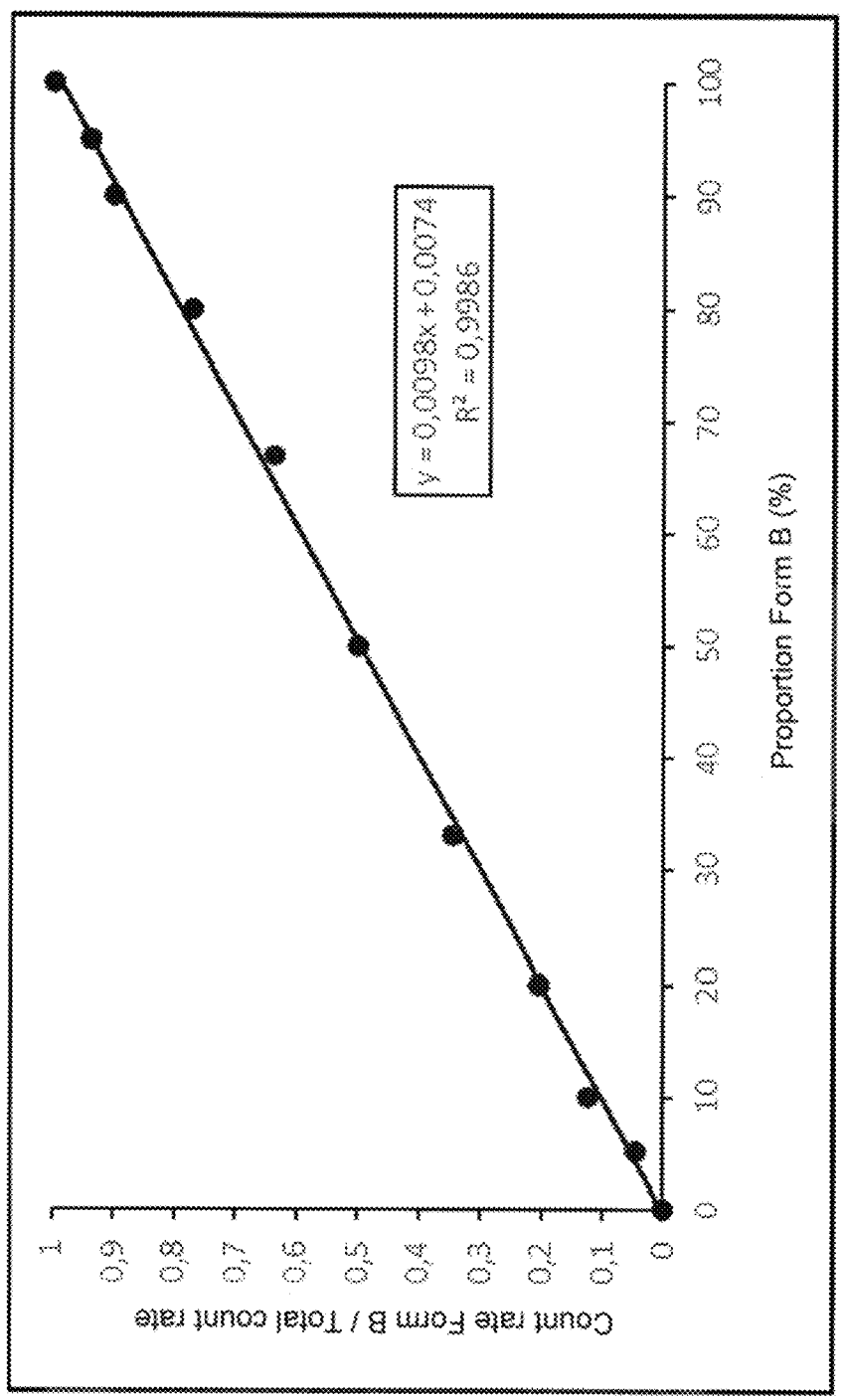
FIG. 9: Calibration curve proportion of crystal form B to crystal form A

XRD data were obtained using mechanical mixtures of pure GAA form A and form B samples. The peak heights at 20.7° and 20.2° were used for quantitative evaluation via the peak height. The calibration curve (calibration line) determined from this with a very good correlation coefficient was used for unknown samples to determine the proportion of form A/B (cf. Table 1 and FIG. 9).

TABLE 1

Calibration curve proportion of crystal form A to crystal form B

| Weight percentage Form B (%) | Weight percentage Form A (%) | X-ray count rate Form A (20.7°) | X-ray count rate Form B (20.2°) | Ratio of count rate B to A + B |
|---|---|---|---|---|
| 0 | 100 | 4000 | 1 | 0.00025 |
| 5 | 95 | 3150 | 150 | 0.04545 |
| 10 | 90 | 3500 | 500 | 0.12500 |
| 20 | 80 | 3500 | 900 | 0.20455 |
| 33 | 67 | 3050 | 1600 | 0.34409 |
| 50 | 50 | 2400 | 2400 | 0.50000 |
| 67 | 33 | 1750 | 3100 | 0.63918 |
| 80 | 20 | 950 | 3250 | 0.77381 |
| 90 | 10 | 400 | 3700 | 0.90244 |
| 95 | 5 | 250 | 4000 | 0.94118 |
| 100 | 0 | 1 | 4100 | 0.99976 |

For the quantitative determination of the ratio of N-(aminoiminomethyl)-2-amino-ethanoic acid crystal form B to crystal form A, mechanical mixtures of powdered samples of the respective pure crystal forms were prepared and measured on the X-ray powder diffractometer. The mixing ratios were 100:0, 95:5, 90:10, 80:20, 67:33, 50:50, 33:67, 20:80, 10:90, 5:95 and 0:100. The signal heights (count rates) at 2theta 20.2° (form B) were related to the sum of the signal heights at 2theta 20.7° (form A) and 2theta 20.2° (form B) and a calibration line was determined from this. With a correlation coefficient $R^2$=0.998, the following linear relationship was found:

$$\text{Weight percent form } B = \left(\left(\frac{\text{count rate form B}}{\text{count rate form A} + \text{count rate form B}}\right) - 0.0074\right) * 102.04$$

This formula was used in the following examples to determine the respective proportions of crystal form A and crystal form B.

Single Crystal X-Ray Structural Analysis

Figure 2:
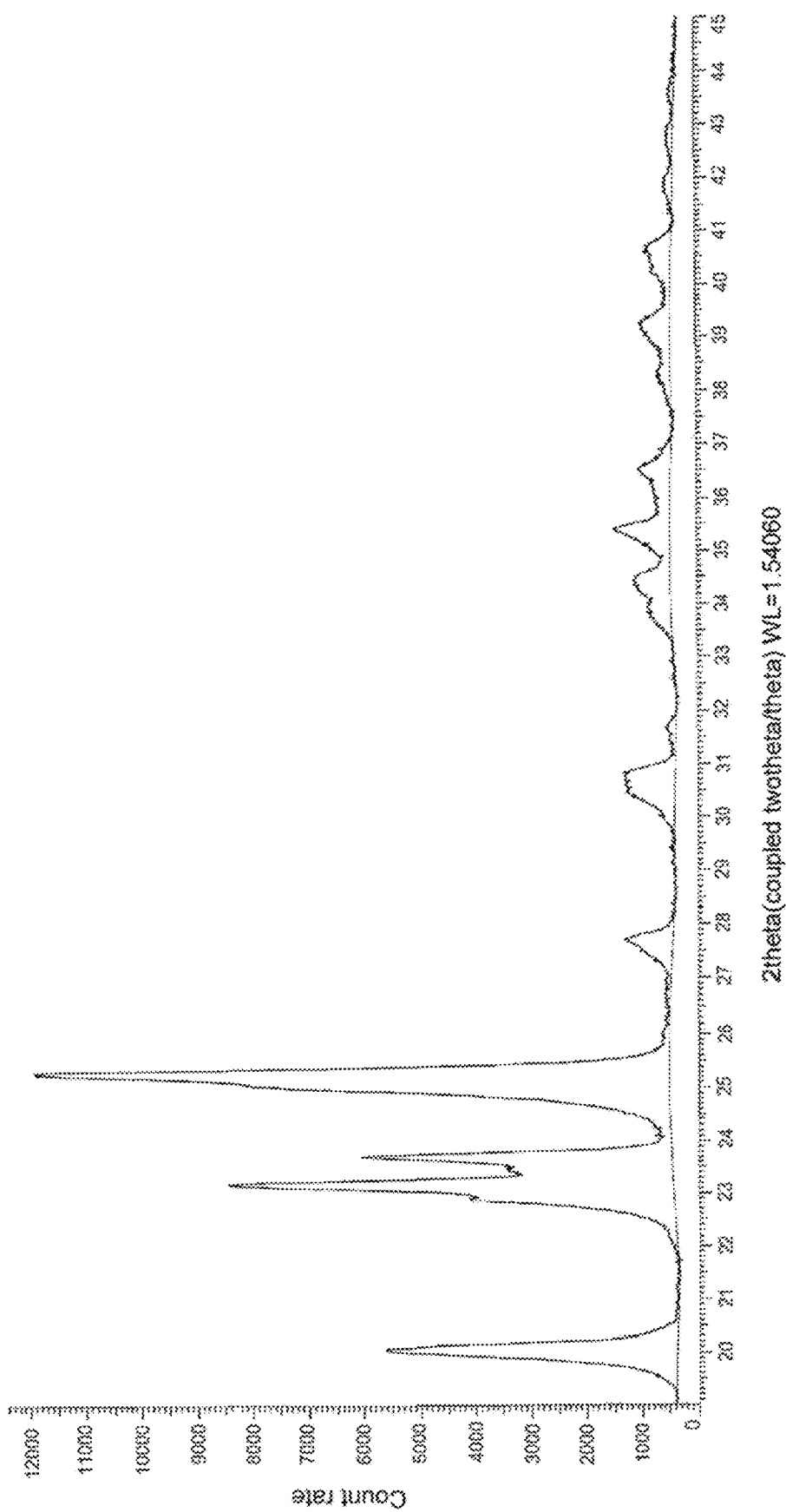
FIG. 2: X-ray powder diffractogram of N-(aminoiminomethyl)-2-aminoacetic acid of form B of Example 2
Figure 6:
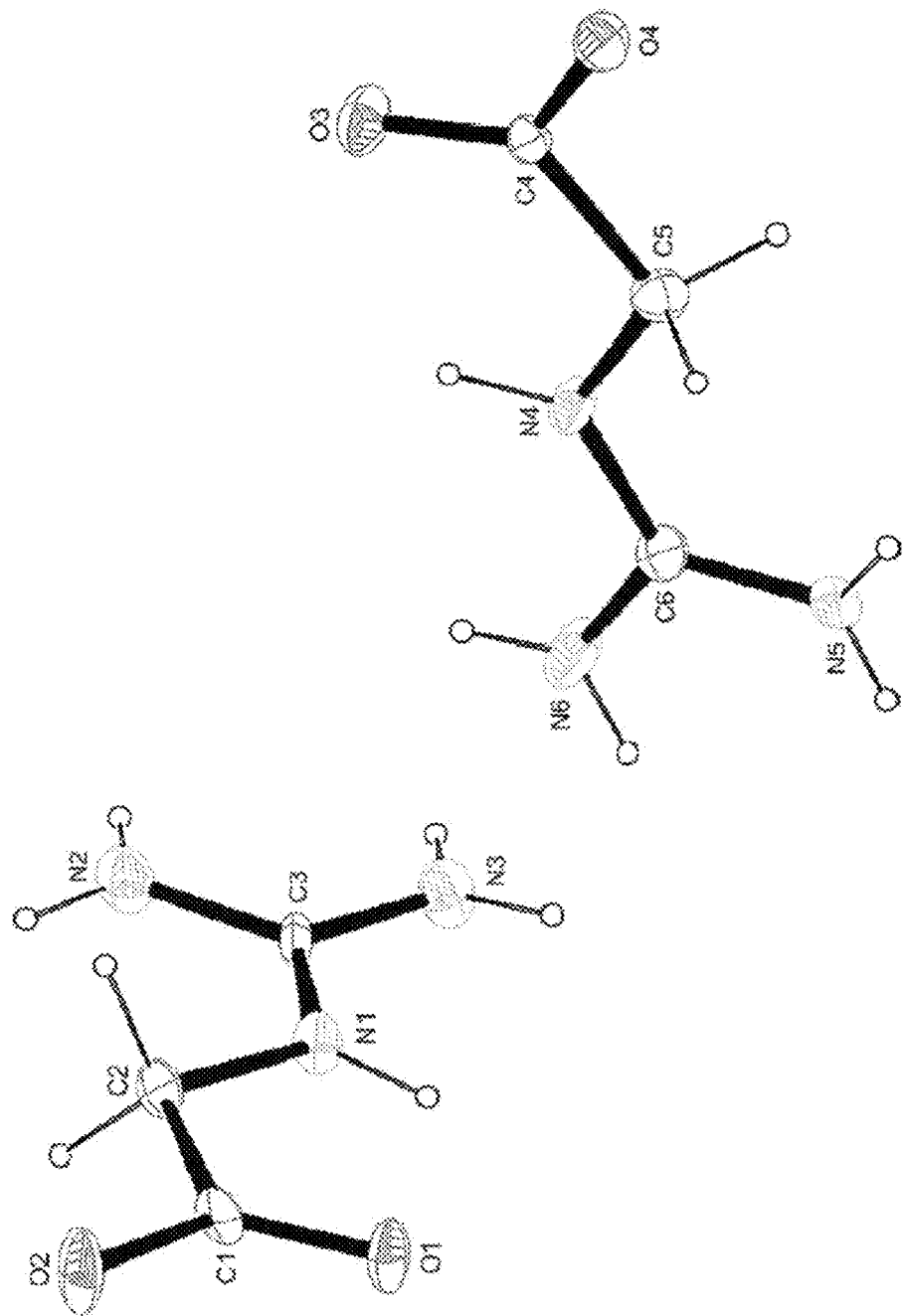
FIG. 6: Illustration of the two crystallographically independent molecules N-(aminoiminomethyl)-2-aminoacetic acid from single crystal X-ray structural analysis
Figure 7:
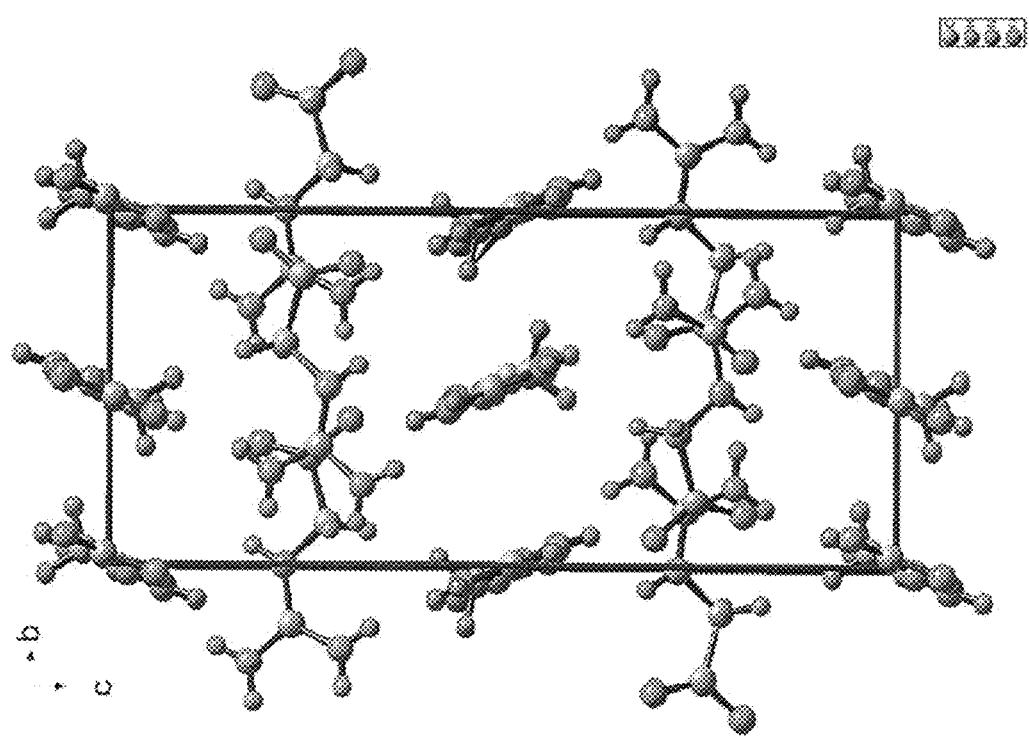
FIG. 7: Illustration of the packing of the molecules of N-(aminoiminomethyl)-2-aminoacetic acid in the crystal structure. The direction of view is along the a-axis. Independent molecular chains arranged perpendicular to each other and bound by H bridges can be clearly seen parallel to the a- and b-axis. These chains are stacked along the c-axis.

A suitable crystal was prepared by evaporating a water-containing solution of N-(aminoiminomethyl)-2-aminoacetic acid in the presence of N,N'-guanidinodiacetic acid. The single crystal measurement was carried out at 105 Kelvin on a crystal of dimension 0.02*0.02*0.09 mm using monochromatic Mo—Kα (molybdenum K-alpha) radiation of wavelength 0.71073 Å using a dual-cycle Bruker D8 Venture TXS diffractometer. Refinement of the X-ray crystal data using 2072 independent reflections was performed by the least square error method up to an R value ($F_{obs}$) of 0.0381. The position of NH and OH hydrogen atoms was refined, and that of CH hydrogen atoms was fixed at the calculated position. The result of the X-ray single crystal structure analysis is illustrated in FIGS. 6 and 7. A powder diffractogram back-calculated from the single crystal structure analysis exactly matched the measured powder diffractogram shown in FIG. 2.

Example 1 (Comparison)—Recrystallization of N-(aminoiminomethyl)-2-aminoacetic Acid From Water 400 g of water was provided at 80° C. and a total of 11.66 g of N-(aminoiminomethyl)-2-aminoacetic acid with a content of 99.0%, present in crystal form A, were dissolved therein spoonwise, the solubility limit being exceeded with the last portion. It was then filtered off at 80° C., the filtrate was mixed with a further 100 g of water and heated to 80° C. A nearly saturated clear solution was formed. By cooling slowly to 20° C. within 4 hours, N-(aminoiminomethyl)-2-aminoacetic acid was crystallized. The precipitated crystals were filtered off and dried at 60° C. in vacuo. 6.51 g of N-(aminoiminomethyl)-2-aminoacetic acid with a content of 99.1% was obtained.

Figure 3:
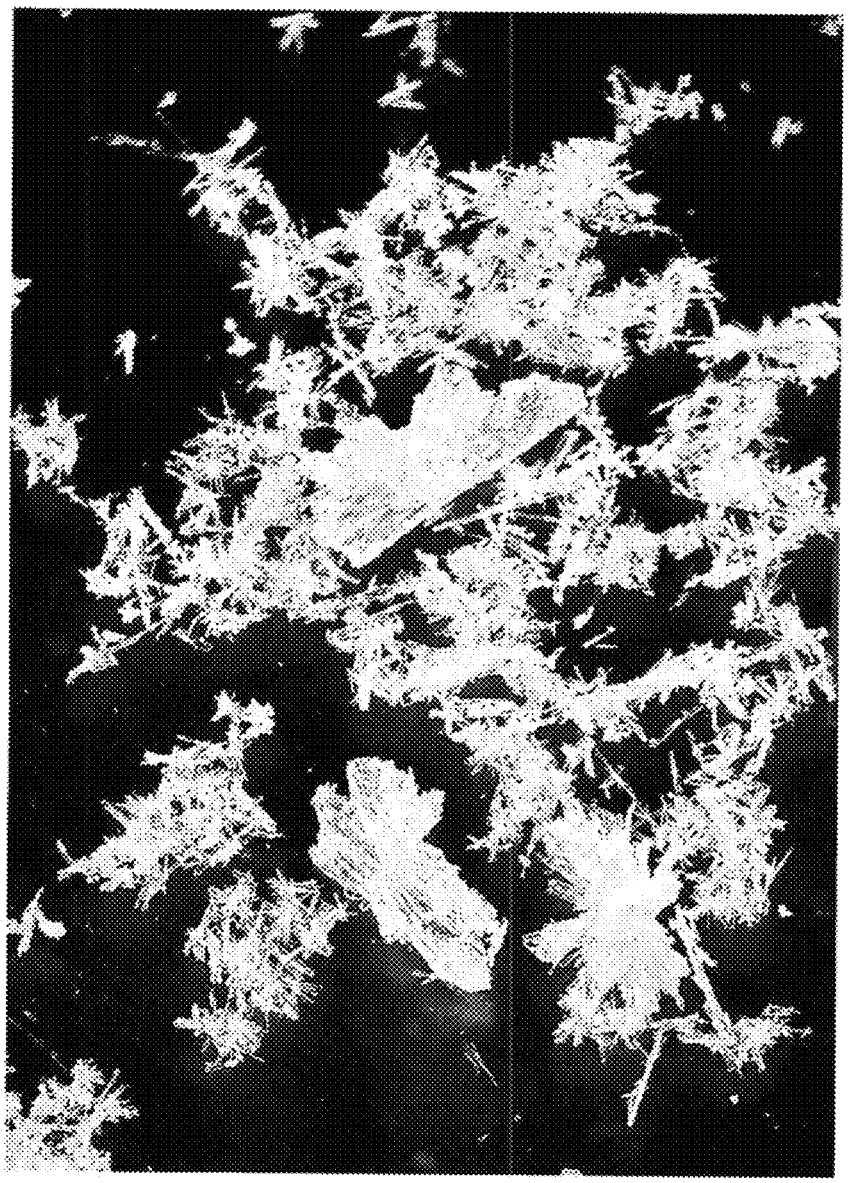
FIG. 3: Photomicrograph of N-(aminoiminomethyl)-2-aminoacetic acid of form A prepared according to Example 1 (image width 8 mm)

The product obtained is in the form of fine acicular crystals. The fine acicular crystals were examined microscopically (see FIG. 3). An X-ray powder diffractometric measurement yielded the powder diffractogram shown in FIG. 1, which indicates the well-known crystal form A.

Example 2—Crystallization of N-(aminoiminomethyl)-2-aminoacetic Acid From a Solution of N,N'-guanidinodiacetic Acid A 1% solution was prepared from 5 g of N,N'-guanidinodiacetic acid from Synthesis Example 2c) and 495 g of water. To 400 g of this solution, N-(aminoiminomethyl)-2-aminoacetic acid of the same composition as in Example 1 was added spoonwise at 80° C. At an added amount of 20.38 g the solubility limit was exceeded. The small solid fraction was filtered off at 80° C., the filtrate was added to the remaining 100 g of the 1% solution of N,N'-guanidinodiacetic acid and stirred at 80° C. for 1 hour. A clear, colorless solution was obtained. By slow cooling to 20° C. within 4 hours, N-(aminoiminomethyl)-2-aminoacetic acid was crystallized. The precipitated crystal aggregates were filtered off, washed 3 times with water at 20° C. and dried at 60° C. 11.67 g of N-(aminoiminomethyl)-2-aminoacetic acid with a content of 99.4% was obtained. The amount obtained is clearly larger than in Example 1, which is due to the increased solubility of N-(aminoiminomethyl)-2-aminoacetic acid caused by the presence of N,N'-guanidinodiacetic acid.

Figure 4:
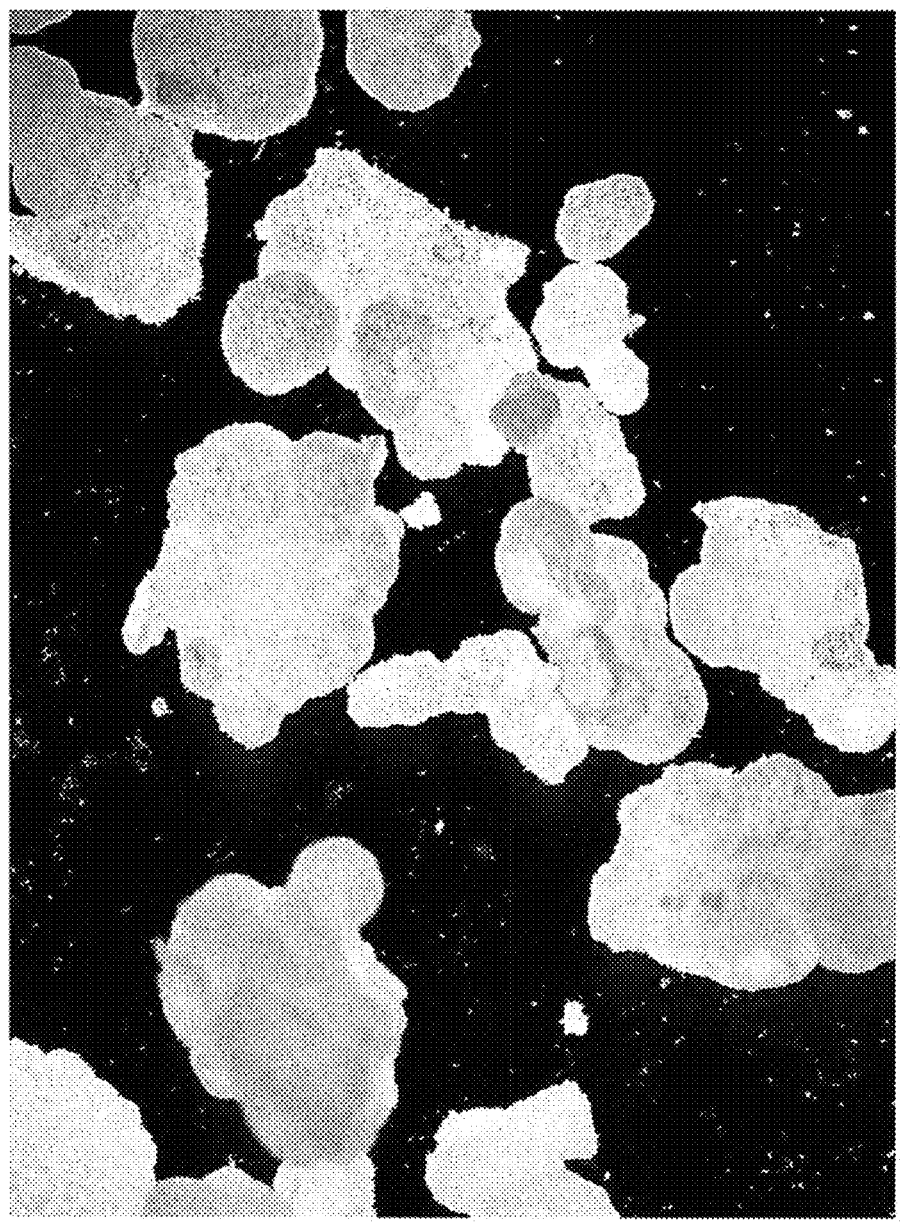
FIG. 4: Photomicrograph of spherical aggregates of N-(aminoiminomethyl)-2-aminoacetic acid of form B, prepared by recrystallization from a solution of N,N'-guanidinodiacetic acid according to Example 2 (image width 8 mm)

An analogously recorded powder diffractogram (see FIG. 2) showed the hitherto unknown crystal form B. The polygonal, roundish crystal aggregates were examined microscopically (see FIG. 4).

Example 3—Recrystallization of N-(aminoiminomethyl)-2-aminoacetic Acid From Water-Containing Solutions of Guanidine Compounds Analogous to Example 2, aqueous solutions of various guanidine compounds were prepared in the respective concentrations (C) indicated. In 400 g of the respective solution, the respective indicated amount (M) of N-(aminoiminomethyl)-2-aminoacetic acid was dissolved at 80° C. After filtration at 80° C., another 100 g of the indicated aqueous solution of the respective guanidine compound was added and the clear solution was stirred at 80° C. for 1 hour. By slow cooling to 20° C. within 4 hours N-(aminoiminomethyl)-2-aminoacetic acid crystallized. The precipitated crystal aggregates were filtered off, washed 3 times with water of 20° C. and dried at 60° C. In each case, the indicated amount (A) of N-(aminoiminomethyl)-2-aminoacetic acid with a content (G) was obtained (see Tables 2a/b).

Powder diffractograms were taken of the respective products and examined for the presence of the respective crystal forms, using the formula given above to determine the proportions of form A and form B.

TABLE 2a

Recrystallization from water-containing solutions of guanidine compounds (not according to the invention)

| No. | Guanidine compound | C % by weight | M g | A g | G % | Crystal form |
|---|---|---|---|---|---|---|
| 3.1 | Melamine | 0.3 | 16.98 | 11.13 | 99.3 | 100% Form A |
| 3.2 | N-cyanoguanidine | 3.0 | 19.80 | 10.09 | 99.1 | 100% Form A |
| 3.3 | L-Arginine | 10.0 | 18.37 | 11.98 | 99.2 | 100% Form A |
| 3.4 | N-(aminoiminomethyl)-N-methyl-2-aminoacetic acid | 1.0 | 17.47 | 8.14 | 99.2 | 100% Form A |
| 3.5 | Biguanide hydrochloride | 50.0 | 13.72 | 7.13 | 99.3 | 100% Form A |
| 3.6 | N,N-dimethylbiguanide | 30.0 | 10.06 | 5.81 | 99.1 | 100% Form A |
| 3.7 | N,N-guanidinodiacetic acid | 2.0 | 18.74 | 10.98 | 99.3 | 100% Form A |
| 3.8 | N,N-guanidinodiacetic acid | 0.5 | 19.62 | 11.05 | 99.4 | 100% Form A |

TABLE 2b

Recrystallization from water-containing solutions of guanidine compounds according to formula (I) - according to the invention

| No. | Guanidine Compound | C % by weight | M g | A g | G % | Crystal form |
|---|---|---|---|---|---|---|
| 3.9 | N,N'-guanidinodiacetic acid | 2.0 | 20.65 | 11.72 | 99.2 | 100% Form B |

TABLE 2b-continued

Recrystallization from water-containing solutions of guanidine compounds according to formula (I) - according to the invention

| No. | Guanidine Compound | C % by weight | M g | A g | G % | Crystal form |
|---|---|---|---|---|---|---|
| 3.10 | N,N'-guanidinodiacetic acid | 0.7 | 20.47 | 11.44 | 99.3 | 97% Form B 3% Form A |
| 3.11 | N,N'-guanidinodiacetic acid | 0.5 | 20.40 | 11.52 | 99.3 | 93% Form B 7% Form A |
| 3.12 | N,N'-guanidinodiacetic acid | 0.2 | 20.38 | 11.63 | 99.4 | 78% Form B 22% Form A |
| 3.13 | N,N'-guanidinodiacetic acid | 01. | 20.32 | 11.49 | 99.4 | 53% Form B 47% Form A |
| 3.14 | N'-carboxymethyl-3-guanidinopropanoic acid | 1.0 | 17.29 | 9.64 | 99.2 | 100% Form B |
| 3.15 | N'-carboxymethyl-4-guanidinobutanoic acid | 1.0 | 16.84 | 8.91 | 99.3 | 100% Form B |

The guanidine compounds according to formula (I) of the invention thus preferentially induce crystal form B during crystallization of N-(aminoiminomethyl)-2-aminoacetic acid, although in some cases mixtures with form A also occur (cf. Table 2b). Other guanidines not according to the invention are not able to do this (cf. Table 2a).

Example 4 (Comparison)—Synthesis of N-(aminoiminomethyl)-2-aminoacetic Acid From Glycine and Cyanamide in Aqueous Solution 112.6 g (1.5 mol) of glycine was dissolved in 300 g of water. To the solution was added 21.6 g (0.27 mol) of a 50% sodium hydroxide solution, resulting in a pH of 8.4. A solution of 42.04 g (1.0 mol) of cyanamide dissolved in 42 g of water was added at 80° C. over the course of 4 hours. The post-reaction was carried out at 80° C. for another hour. The obtained suspension was cooled to 20° C., filtered off, washed with water and dried at 60° C. 100.6 g N-(amino-iminomethyl)-2-aminoacetic acid with a content of 99.1% was obtained. The yield was 85.9%.

A powder diffractogram of the obtained fine acicular crystals indicated the sole presence of form A (100% form A).

Example 5 (According to the Invention)—Synthesis of N-(aminoiminomethyl)-2-aminoacetic Acid From Glycine and Cyanamide in a 2% Solution of N,N'-guanidinodiacetic Acid A solution was prepared from 6 g of N,N'-guanidinodiacetic acid and 294 g of water. Dissolved therein were 112.6 g (1.5 mol) of glycine and a pH of 8.4 was adjusted with 22.7 g (0.28 mol) of a 50% sodium hydroxide solution. A solution of 42.04 g (1.0 mol) of cyanamide dissolved in 42 g of water was added at 80° C. over the course of 4 hours. The post-reaction was carried out at 80° C. for another hour. The obtained suspension was cooled to 20° C., filtered off, washed with water and dried at 60° C. 99.6 g of N-(aminoiminomethyl)-2-aminoacetic acid containing 99.3% was obtained. The yield was 85.0%.

A powder diffractogram of the obtained crystals showed that only N-(aminoiminomethyl)-2-aminoacetic acid of crystal form B (100% form B) was present.

Example 6 (Comparison)—Synthesis of N-(aminoiminomethyl)-2-aminoacetic Acid From Glycine and Cyanamide in a Solution of Different Substances A stock solution A was prepared from a mixture of different substances. This comprised:
30 g N-cyanoguanidine
30 g hydantoic acid
10 g urea
5 g glycylglycine
5 g glycocyamidine
0.5 g melamine These substances were dissolved in water and the mixture was made up to a total weight of 1000 g.

In 300 g of this stock solution A, 112.6 g (1.5 mol) of glycine was dissolved and a pH of 8.4 was adjusted with 20.9 g (0.26 mol) of a 50% sodium hydroxide solution. A solution of 42.04 g (1.0 mol) of cyanamide dissolved in 42 g of water was added at 80° C. over the course of 4 hours. The post-reaction was carried out at 80° C. for another hour. The obtained suspension was cooled to 20° C., filtered off, washed with water and dried at 60° C. 100.5 g N-(amino-iminomethyl)-2-aminoacetic acid containing 99.0% was obtained. The yield was 85.8%.

A powder diffractogram of the crystals obtained showed that only form A was present.

Example 7 (According to the Invention)—Synthesis of N-(aminoiminomethyl)-2-aminoacetic Acid From Glycine and Cyanamide in a Solution of Various Substances Involving Guanidine Compounds According to the Invention A stock solution B was prepared from a mixture of different substances. This comprised:
30 g N-cyanoguanidine
30 g hydantoic acid
10 g urea
5 g glycylglycine
5 g glycocyamidine
0.5 g melamine
15 g N,N'-guanidinodiacetic acid These substances were dissolved in water and the mixture was made up to a total weight of 1000 g. Compared with stock solution A, stock solution B thus contained an additional 1.5% by weight of N,N'-guanidinodiacetic acid.

In 300 g of this stock solution B, 112.6 g (1.5 mol) of glycine were dissolved and a pH of 8.4 was adjusted with 21.3 g (0.27 mol) of a 50% sodium hydroxide solution. A solution of 42.04 g (1.0 mol) of cyanamide dissolved in 42 g of water was added at 80° C. over the course of 4 hours. The post-reaction was carried out at 80° C. for another hour. The obtained suspension was cooled to 20° C., filtered off, washed with water and dried at 60° C. 100.7 g of N-(aminoiminomethyl)-2-aminoacetic acid containing 99.2% was obtained. The yield was 86.0%.

A powder diffractogram of the crystals obtained showed that only form B was present.

Thus, the presence of N,N'-guanidinodiacetic acid causes crystallization of N-(aminoiminomethyl)-2-aminoacetic acid in crystal form B even in a complex mixture of substances.

Example 8 Recrystallization of N-(aminoiminomethyl)-2-aminoacetic Acid From Different Concentrations of Stock Solution B Different initial concentrations were prepared from x g of stock solutions A and B from Examples 10 and 11, respectively, and y g of water (see table). N-(aminoiminomethyl)-2-aminoacetic acid was added by the spoonful to 400 g of each of these solutions at 80° C. The amount (S) required to reach the saturation limit in each case is given in the table. Then filtering was carried out at 80° C., another 100 g of the respective solution was added to the filtrate and stirred at 80° C. for 1 hour. By slowly cooling to 20° C. within 4 hours, N-(aminoiminomethyl)-2-aminoacetic acid was crystallized. The precipitated product was filtered off, washed with water and dried at 60° C. The respective weights (A) of N-(aminoiminomethyl)-2-aminoacetic acid are shown in the table.

The powdered products were analyzed for their crystal form by powder diffraction. The results are summarized in Table 3.

TABLE 3

Recrystallization from stock solutions B

| Nr. | Stock solution | x g | y g | S g | A g | Obtained crystal form |
|---|---|---|---|---|---|---|
| 8.1 | A | 500 | 0 | 20.7 | 13.34 | 100% crystal form A |
| 8.2 | A | 250 | 250 | 19.53 | 13.17 | 100% crystal form A |
| 8.3 | B | 500 | 0 | 19.49 | 12.12 | 100% crystal form B |
| 8.4 | B | 250 | 250 | 22.16 | 12.26 | 100% crystal form B |
| 8.5 | B | 125 | 375 | 18.18 | 12.73 | 100% crystal form B |
| 8.6 | B | 50 | 450 | 19.40 | 13.16 | Mixture of crystal forms A and B with 46% form B, 54% form A |
| 8.7 | B | 25 | 475 | 23.72 | 12.11 | 100% crystal form A |

The result clearly shows that the N,N'-guanidinodiacetic acid additionally contained in stock solution B causes the crystallization of N-(aminoiminomethyl)-2-aminoacetic acid in form B. At higher dilution, this effect is gradually lost.

Example 9—Physicochemical Characterization of N-(aminoiminomethyl)-2-aminoacetic Acid of Form A and Form B 9.1 Melting or Decomposition Point A Mettler DSC 3+ instrument with 40 µl aluminum crucible was used for Dynamic Differential Scanning calorimetry (DSC). The heating rate was 10 Kelvin per minute at a temperature range of 30 to 350° C. Approximately 1.4 mg each of the products of Examples 1 and 2 were weighed into aluminum crucibles and measured at atmospheric pressure (960 mbar at an altitude of 500 m above sea level).

Figure 10:
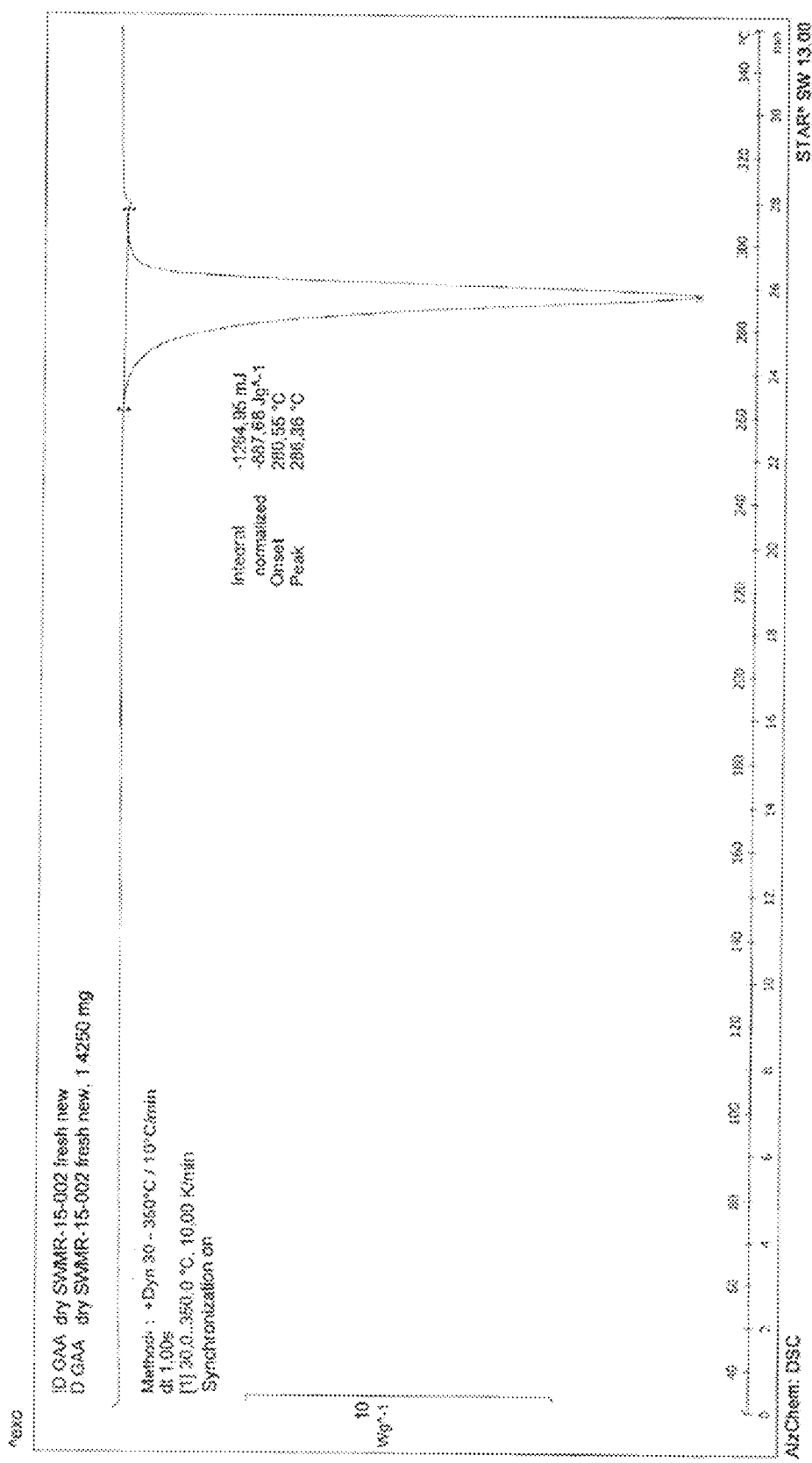
FIG. 10: DSC N-(aminoiminomethyl)-2-aminoacetic acid form A

The sample of Example 1 (=N-(aminoiminomethyl)-2-aminoacetic acid of form A) showed an onset (inflection point of the melting curve projected onto the baseline) of 280.5° C. and a peak temperature of the melting curve of 286.3° C. The total endothermic heat of fusion was 887 J/g (cf. FIG. 10). The product turned from white to brown during melting.

Figure 11:
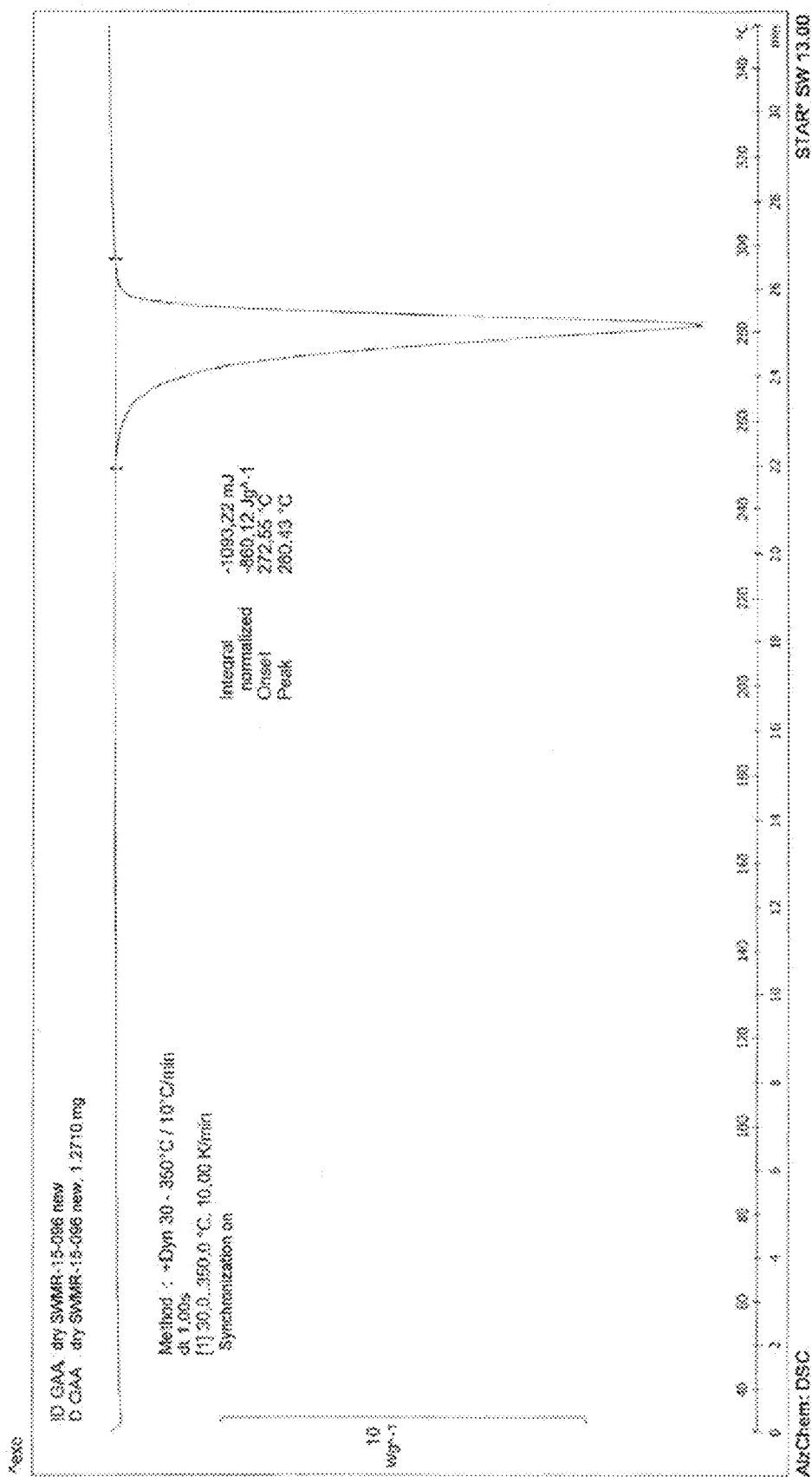
FIG. 11: DSC N-(aminoiminomethyl)-2-aminoacetic acid form B

The sample of Example 2 (=N-(aminoiminomethyl)-2-aminoacetic acid form B) was measured analogously. It showed an onset of 272.5° C. and a peak at 280.4° C., the heat of fusion was 860 J/g, the discoloration was identical (see FIG. 11).

Form B thus melts approx. 6 to 8 Kelvin lower than form A and has a 27 J/g lower heat of fusion or 27 J/g higher lattice energy. In other words, 27 J/g less energy is required for form B than for form A in order to achieve the same energy melting state. Form B thus represents a metastable crystal form or a polymorph of N-(aminoiminomethyl)-2-aminoacetic acid that is higher in energy under normal pressure and temperature conditions.

This new metastable crystal modification form B is stable up to its melting point. A solid transformation from form B to form A or a reversible solid transformation of form A/form B cannot be observed. Thus, form B is an example of monotropic polymorphism.

Figure 5:
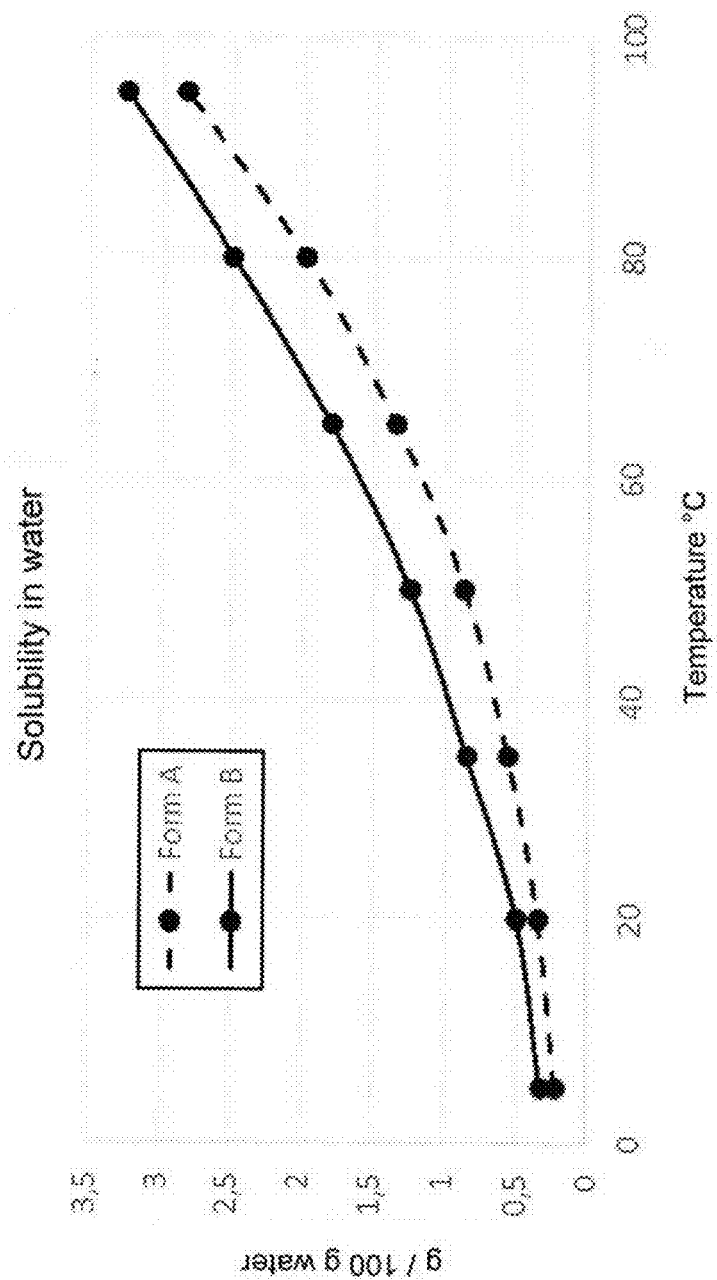
FIG. 5: Solubility curve of N-(aminoiminomethyl)-2-aminoacetic acid of form A and form B, respectively, in water

9.2 Determination of Water Solubility 100 g of water at 5° C. were provided. The product of Example 1 (=N-(aminoiminomethyl)-2-aminoacetic acid form A) was dissolved therein until saturation was reached and the dissolved amount was determined by backweighing. Then the temperature was increased to 20° C. and as much of the sample was added until the saturation point was reached again. The same was repeated at further temperatures, maximum at 95° C. An analogous measurement was made with the product of Example 2 (=N-(aminoiminomethyl)-2-aminoacetic acid form B). The solubility data obtained for both products were summarized graphically in FIG. 5.

Both crystal forms of N-(aminoiminomethyl)-2-aminoacetic acid dissolve better in water with increasing temperature. The inventive N-(aminoiminomethyl)-2-aminoacetic acid form B dissolves about 20% better than the known form A at any temperature.

9.3 Determination of Density

Crystals of N-(aminoiminomethyl)-2-aminoacetic acid form A of Example 1 were introduced into tetrachloromethane at 20° C., where they floated on the surface. By adding dichloromethane dropwise, the density of the liquid medium was decreased until the crystals just started to float in the liquid without rising and without sinking to the bottom. The density of the liquid phase was determined in a pycnometer. A density of 1.50+/−0.03 g/cm$^3$ was measured.

The same procedure was followed with crystals of form B of Example 2. The density at 20° C. was determined to be 1.41+/−0.03 g/cm$^3$.

Form B thus has a 6% lower density than form A. This correlates with the lower lattice energy of form B determined above. The measured crystal densities also agree with the X-ray crystal densities calculated from the respective lattice constants.

9.4 Determination of Dust Content

The product of Example 1 was sieved through a sieve with mesh size 63 µm (equivalent to 230 mesh–mesh size). 46 wt. % fines were obtained. An analogous procedure was followed with the sample of Example 2 consisting of polygonal, roundish crystal aggregates. Here, a fines content of less than 3 wt. % was determined. Low-dust materials, which can therefore be handled safely, should have a dust content (i.e. grain content<63 µm) of less than 10%. The product of Example 2 (N-(aminoiminomethyl)-2-aminoacetic acid of crystal form B) satisfies this, while Comparative Example 1 (N-(aminoiminomethyl)-2-aminoacetic acid of crystal form A) does not.

9.5 Determination of the Angle of Repose

The product of Example 1, consisting of matted acicular crystals, was poured through a funnel onto a flat surface using a device according to DIN ISO 4324. After removing the funnel, the angle of repose of the cone obtained was determined with an angle measuring device. It was approximately 45°. Accordingly, N-(aminoiminomethyl)-2-aminoacetic acid form A exhibits poor flow behavior. The granular product of Example 2 was measured anlogously. Here, a repose angle of about 25° was obtained. N-(aminoiminomethyl)-2-aminoacetic acid form B thus exhibits excellent flow behavior.

9.6 Determination of Bulk Density

A weighed quantity of the product of Example 1 was placed in a measuring cylinder and partially compacted by tapping it firmly twice on the laboratory bench. From the filling level of the measuring cylinder, the bulk density was determined to be 0.37 g/cm³. The same procedure was followed with the product of Example 2. Here, a bulk density of 0.62 g/cm³ was determined. N-(aminoiminomethyl)-2-aminoacetic acid of form B thus has a significantly increased bulk density, which is advantageous for packaging, transport and handling of the product.

9.7 Thermal Stability of N-(aminoiminomethyl)-2-aminoacetic Acid Form B a) N-(aminoiminomethyl)-2-aminoacetic acid form B of Example 2 was placed in the drying oven for 6 hours at 120° C. X-ray powder diffraction was then used to determine the crystal form. This remained unchanged pure crystal form B.

b) N-(aminoiminomethyl)-2-aminoacetic acid form B of Example 2 was wetted with 20% water, incubated for 6 hours at 65° C. in a closed vessel, then dried. The X-ray powder diffractogram showed no change, form B remained stable.

c) N-(aminoiminomethyl)-2-aminoacetic acid form B of Example 2 was prepared as a 10% suspension in water. This suspension was stirred at 80° C. for 2 hours. It was then cooled, the solid filtered off and dried. X-ray powder diffraction showed that a mixture of crystals forms A and B was present.

d) N-(aminoiminomethyl)-2-aminoacetic acid form B of Example 2 was dissolved in water at 80° C., largely recrystallized by cooling the solution, filtered off and dried. X-ray powder diffraction yielded pure crystal form A.

N-(aminoiminomethyl)-2-aminoacetic acid form B is thus very stable in solid form, but has a tendency to change to crystal form A via the water-containing solution. This behavior also confirms the metastable crystal structure of form B.

9.8 Physical Property of Mixtures of Form A and Form B

In Example 9.6, the bulk density of GAA form A was determined to be 0.37 g/cm³ and that of GAA form B 0.62 g/cm³. Starting from pure substance samples of GAA form A or form B, mixtures of the two forms were weighed in and mixed by shaking (not grinding or mortaring!). The bulk densities of the crystal mixtures produced in this way were determined.

TABLE 4

Bulk density in the crystal mixture

| Weight proportion Form A | Weight proportion Form B | Bulk density |
|---|---|---|
| 100% | 0% | 0.62 g/cm³ |
| 75% | 25% | 0.59 g/cm³ |
| 50% | 50% | 0.53 g/cm³ |
| 25% | 75% | 0.41 g/cm³ |
| 0% | 100% | 0.37 g/cm³ |

Figure 8:
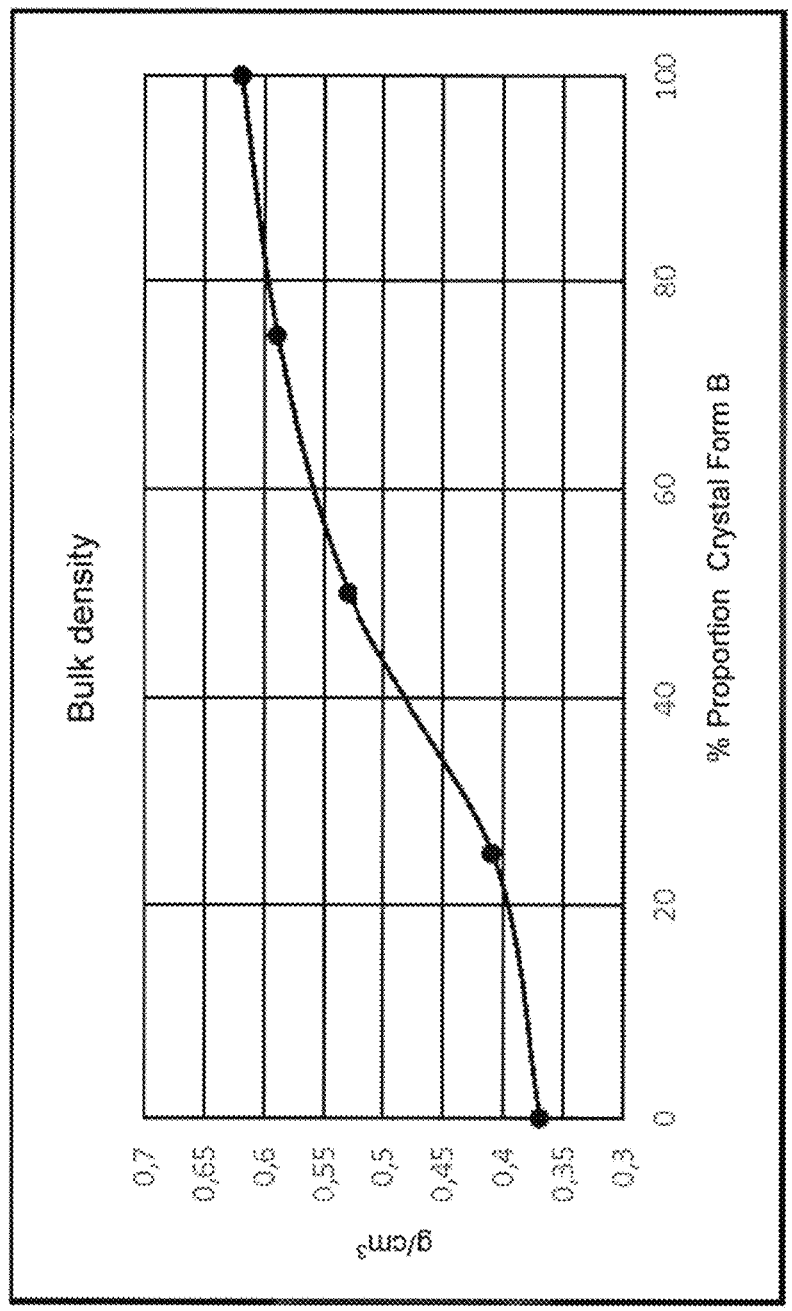
FIG. 8: Bulk density depending on concentration form B

It can be seen that the bulk density increases as the proportion of GAA form B increases, whereby from 50% form B the bulk density is advantageously above the arithmetic mean of the two end members (cf. also FIG. 8).

The invention claimed is:

1. A process for preparing N-(aminoiminomethyl)-2-aminoacetic acid comprising N-(aminoiminomethyl)-2-aminoacetic acid in a thermodynamically metastable crystal modification, wherein the thermodynamically metastable crystal modification shows in the X-ray powder diffractogram of the crystal modification when using Cu—Kα radiation the strongest reflection bands at 2Θ=20.2° and 23.3° and 23.8° and 25.3° with a measurement accuracy of +/−0.2°, wherein N-(aminoiminomethyl)-2-aminoacetic acid is crystallized from a water-containing solution in the presence of at least one guanidine compound of formula (I), wherein formula (I) represents:

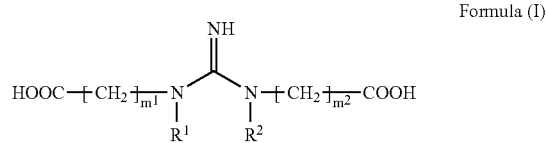

Formula (I)

where radicals $R^1$, $R^2$ as well as indices $m^1$, $m^2$ in formula (I) independently of one another mean:
$R^1$, $R^2$=independently of one another hydrogen or $C_1$ to $C_4$ alkyl,
$m^1$, $m^2$=independently of one another 1, 2 or 3,
wherein the guanidine compounds of formula (I) are present in an amount of at least 0.01 wt-% (based on the total weight of the solution).

2. The process according to claim 1, wherein the water-containing solution contains at least 40% by weight of water (based on the total weight of the solution).

3. The process according to claim 1, wherein N-(aminoiminomethyl)-2-aminoacetic acid is dissolved in water or a water-containing solution in a first process step, and the N-(aminoiminomethyl)-2-aminoacetic acid comprising N-(aminoiminomethyl)-2-aminoacetic acid in a thermodynamically metastable crystal modification is crystallized in a second process step from the solution prepared in the first process step in the presence of the guanidine compound of formula (I).

4. The process according to claim 1, wherein N-(aminoiminomethyl)-2-aminoacetic acid is prepared in a first process step from cyanamide and glycine in water or in a water-containing solution, and the N-(aminoiminomethyl)-2-aminoacetic acid comprising N-(aminoiminomethyl)-2-aminoacetic acid in a thermodynamically metastable crystal modification is crystallized in a second process step from the reaction mixture prepared in the first process step in the presence of the guanidine compound of formula (I).

5. The process according to claim 1, wherein N-(amino-iminomethyl)-2-aminoacetic acid is dissolved or prepared in the water-containing solution in the first process step at a temperature in the range of 20 to 100° C. at normal pressure.

6. The process according to claim 1, wherein the guanidine compounds of formula (I) are used in an amount corresponding to 80% of the maximum amount which can be dissolved in water at 25° C. under normal pressure.

7. The process according to claim 1, wherein the thermodynamically metastable crystal modification has the orthorhombic space group $P2_12_12_1$ with Z=8 with lattice constants a=7.7685 Å, b=7.7683 Å and c=17.4261 Å at 105 Kelvin and a measurement accuracy of +/−0.001 Å.

* * * * *